United States Patent [19]
Taniguchi et al.

[11] Patent Number: 5,831,006
[45] Date of Patent: Nov. 3, 1998

[54] FACTOR REGULATING GENE EXPRESSION

[75] Inventors: Tadatsugu Taniguchi, Ibaraki; Takashi Fujita, Aogein 4-18-12, Mino-shi, Osaka 562, both of Japan

[73] Assignee: Takashi Fujita, Osaka, Japan

[21] Appl. No.: 414,301

[22] Filed: Mar. 31, 1995

Related U.S. Application Data

[62] Division of Ser. No. 347,251, Nov. 18, 1994, Pat. No. 5,616,699, which is a continuation of Ser. No. 87,465, Jul. 8, 1993, abandoned, which is a continuation of Ser. No. 397,967, Aug. 24, 1989, abandoned.

[30] Foreign Application Priority Data

Nov. 24, 1986 [EP] European Pat. Off. ............ 881196026
Aug. 24, 1988 [EP] European Pat. Off. ............ 881137939

[51] Int. Cl.$^6$ .......................... C07K 14/47; C12P 21/02; C12N 15/70; C12N 15/79
[52] U.S. Cl. ........................ 530/350; 435/69.1; 435/70.1; 435/71.1; 435/257.33; 435/370.1; 536/23.1; 536/24.1
[58] Field of Search ................................ 536/23.1, 23.5, 536/23.52, 24.1; 435/69.1, 69.5, 69.51, 70.1, 71.1, 320.1, 252.3, 252.33; 935/22, 23; 530/350

[56] References Cited

U.S. PATENT DOCUMENTS 5,616,699  4/1997  Taniguchi et al. ...................... 536/23.1

OTHER PUBLICATIONS

Au, W.–C. et al., "Distinct activation of murine interferon–α promoter region by IRF–1/ISFG–2 and virus infection," *Nuc. Acids Res.* 20(11):2877–2884 (Jun. 1992).

Clark, S.C. and R. Kamen, "The Human Hematopoietic Colony–Stimulating Factors," *Science* 236:1229–1237 (Jun. 1987).

Dinter, H. and H. Hauser, "Cooperative interaction of multiple DNA elements in the human interferon–β promoter," *Eur. J. Biochem.* 166(1):103–109 (Jul. 1987).

Fujita, T. et al., "Delimitation and Properties of DNA Sequences Required for the Regulated Expression of Human Interferon–β Gene," *Cell* 41:489–496 (1985).

Fujita, T. et al., "Interferon–β Gene Regulation: Tandemly Repeated Sequences of a Synthetic 6 bp Oligomer Function As a Virus–Inducible Enhancer," *Cell* 49(3):357–367 (May 1987).

Fujita, T. et al., "Evidence for a nuclear factor(s), IRF–1, mediating induction and silencing properties to human IFN–β gene regulatory elements," *EMBO J.* 7(11):3397–3405 (Nov. 1988).

Fujita, T. et al., "Induction of endogenous IFN–α and IFN–β genes by a regulatory transcription factor, IRF–1," *Nature* 337:270–272 (Jan. 1989).

Harada, H. et al., "Structurally Similar but Functionally Distinct Factors, IRF–1 and IRF–2, Bind to the Same Regulatory Elements of IFN and IFN–Inducible Genes," *Cell* 58:729–739 (Aug. 1989).

Harada, H. et al., "Absence of the Type I IFN System in EC Cells: Transcriptional Activator (IRF–1) and Repressor (IRF–2) Genes Are Developmentally Regulated," *Cell* 63(2):303–312 (Oct. 1990).

Kelller, A.D. and T. Maniatis, "Identification of an inducible factor that binds to a positive regulatory element of the human β–interferon gene," *Proc. Natl. Acad. Sci. USA* 85:3309–3313 (May 1988).

Klemm, U. et al., "Rat sperm acrosin: cDNA sequence, derived primary structure and phylogenetic origin," *Biochem. Biophy. Acta* 1090(2):270–272 (Oct. 1991).

Levy, D. et al., "Interferon–induced nuclear factors that bind a shared promoter element correlate with positive and negative transcriptional control," *Genes & Dev.* 2:383–393 (Apr. 1988).

Maniatis, T. et al., "Regulation of Inducible and Tissue–Specific Gene Expression," *Science* 236:1237–1245 (Jun. 1987).

Miyamoto, M. et al., "Regulated Expression of a Gene Encoding a Nuclear Factor, IRF–1, That Specifically Binds to IFN–β Gene Regulatory Elements," *Cell* 54:903–913 (Sep. 1988).

Näf, D. et al., "Multimerization of AAGTGA and GAAAGT generates sequences that mediate virus inducibility by mimicking an interferon promoter element," *Proc. Natl. Acad. Sci. USA* 88(4):1369–1373 (Feb. 1991).

Reis, L.F.I. et al., "Critical role of a common transcription factor, IRF–1, in the regulation of IFN–β and IFN–inducible genes," *EMBO J.* 11(1):185–193 (Jan. 1992).

Stark, G.R. and I.M. Kerr, "Interferon–Dependent Signaling Pathways: DNA Elements, Transcription Factors, Mutations, and Effects of Viral Proteins," *J. Interfer. Res.* 12:147–151 (Jun. 1992).

Taniguchi, T. et al., "Regulation of Cytokine Gene Expression," *Ann. Rev. Immunol.* 6:439–464 (Apr. 1988).

Watanabe, N. et al., "Activation of IFN–β element by IRF–1 requires a post–translational event in addition to IRF–1 synthesis," *Nuc. Acids Res.* 19(16):4421–4428 (Aug. 1991).

Yamada, G. et al., "Specific depletion of the B–cell population induced by aberrant expression of human interferon regulatory factor 1 gene in transgenic mice," *Proc. Natl. Acad. Sci. USA* 88(2):532–536 (Jan. 1991).

Fujita et al. "Structure, Function & Regulation of a Gene Encoding Transcription Factor, IRF, That Mediats IFN–β Gene Expression" J. Interferon Res. 8(Suppl. 1):S3 1988.

Taniguchi et al. "Regulatory Cis–Elements & Trans–Acting Factors in Cytokine Gene Expression" J. Interferon Res. 8(Suppl. 1):S1 1988.

*Primary Examiner*—Nancy Degen
*Attorney, Agent, or Firm*—Sterne, Kessler, Goldstein & Fox P.L.L.C.

[57] ABSTRACT

A recombinant DNA molecule coding for a protein having the activity of an interferon regulatory factor-1 (IRF-1).

16 Claims, 15 Drawing Sheets

FIG. 4A

```
  1 GGACGTGCTTTCACAGTCTAAGCCGAACCGAACCGAACCGAACCGAACCGGGCC

60 GAGTTGCGCCGAGGTCAGCCGAGGTGGCCAGAGGACCCCAGCATCTCGGGCATCTTTCG

119 CTTCGTGCGCGCATCGCGTACCTACACCGCAACTCCGTGCCTCGCTCTCCGGCACCCTC

λL28-8   1
                                             Met Pro Ile Thr Arg Met Arg
178 TGCGAATCGCTCCTGCAGCAA         AGCCACC ATG CCA ATC ACT CGA ATG CGG

20
    Met Arg Pro Trp Leu Glu Met Gln Ile Asn Ser Asn Gln Ile Pro
227 ATG AGA CCC TGG CTA GAG ATG CAG ATT AAT TCC AAC CAA ATC CCA

Gly Leu Ile Trp Ile Asn Lys Glu Glu Met Ile Phe Gln Ile Pro
272 GGG CTG ATC TGG ATC AAT AAA GAA GAG ATG ATC TTC CAG ATT CCA

40
    Trp Lys His Ala Ala Lys His Gly Trp Asp Ile Asn Lys Asp Ala
317 TGG AAG CAC GCT GCT AAG CAC GGC TGG GAC ATC AAC AAG GAT GCC

60
    Cys Leu Phe Arg Ser Trp Ala Ile His Thr Gly Arg Tyr Lys Ala
362 TGT CTG TTC CGG AGC TGG GCC ATT CAC ACA GGC CGA TAC AAA GCA

80
    Gly Glu Lys Glu Pro Asp Pro Lys Thr Trp Lys Ala Asn Phe Arg
407 GGA GAA AAA GAG CCA GAT CCC AAG ACA TGG AAG GCA AAC TTC CGT

Cys Ala Met Asn Ser Leu Pro Asp Ile Glu Glu Val Lys Asp Gln
452 TGT GCC ATG AAC TCC CTG CCA GAC ATC GAG GAA GTG AAG GAT CAG
              100
    Ser Arg Asn Lys Gly Ser Ser Ala Val Arg Val Tyr Arg Met Leu
497 AGT AGG AAC AAG GGC AGC TCT GCT GTG CCG GTG TAC CGG ATG CTG
                              120
    Pro Pro Leu Thr Arg Asn Gln Arg Lys Glu Arg Lys Ser Lys Ser
542 CCA CCC CTC ACC AGG AAC CAG AGG AAA GAG AGA AAG TCC AAG TCC
                                                      140
    Ser Arg Asp Thr Lys Ser Lys Thr Lys Arg Lys Leu Cys Gly Asp
587 AGC CGA GAC ACT AAG AGC AAA ACC AAG AGG AAG CTG TGT GGA GAT

Val Ser Pro Asp Thr Phe Ser Asp Gly Leu Ser Ser Ser Thr Leu
632 GTT AGC CCG GAC ACT TTC TCT GAT GGA CTC AGC AGC TCT ACC CTA
```

```
            160
    Pro Asp Asp His Ser Ser Tyr Thr Thr Gln Gly Tyr Leu Gly Gln
677 CCT GAT GAC CAC AGC AGT TAC ACC ACT CAG GGC TAC CTG GGT CAG

180
    Asp Leu Asp Met Glu Arg Asp Ile Thr Pro Ala Leu Ser Pro Cys
722 GAC TTG GAT ATG GAA AGG GAC ATA ACT CCA GCA CTG TCA CCG TGT

200
    Val Val Ser Ser Ser Leu Ser Glu Trp His Met Gln Met Asp Ile
767 GTC GTC AGC AGC AGT CTC TCT GAG TGG CAT ATG CAG ATG GAC ATT

Ile Pro Asp Ser Thr Thr Asp Leu Tyr Asn Leu Gln Val Ser Pro
812 ATA CCA GAT AGC ACC ACT GAT CTG TAT AAC CTA CAG GTG TCA CCC

220
    Met Pro Ser Thr Ser Glu Ala Ala Thr Asp Glu Asp Glu Glu Gly
857 ATG CCT TCC ACC TCC GAA GCC GCA ACA GAC GAG GAT GAG GAA GGG

240
    Lys Ile Ala Glu Asp Leu Met Lys Leu Phe Glu Gln Ser Glu Trp
902 AAG ATA GCC GAA GAC CTT ATG AAG CTC TTT GAA CAG TCT GAG TGG

260
    Gln Pro Thr His Ile Asp Gly Lys Gly Tyr Leu Leu Asn Glu Pro
947 CAG CCG ACA CAC ATC GAT GCC AAG GGA TAC TTG CTC AAT GAG CCA

Gly Thr Gln Leu Ser Ser Val Tyr Gly Asp Phe Ser Cys Lys Glu
992 GGG ACC CAG CTC TCT TCT GTC TAT GGA GAC TTC AGC TGC AAA GAG

280
    Glu Pro Glu Ile Asp Ser Pro Arg Gly Asp Ile Gly Ile Gly Ile
1037 GAA CCA GAG ATT GAC AGC CCT CGA GGG GAC ATT GGG ATA GGC ATA

300
    Gln His Val Phe Thr Glu Met Lys Asn Met Asp Ser Ile Met Trp
1082 CAA CAT GTC TTC ACG GAG ATG AAG AAT ATG GAC TCC ATC ATG TGG

320
    Met Asp Ser Leu Leu Gly Asn Ser Val Arg Leu Pro Pro Ser Ile
1127 ATG GAC AGC CTG CTG GGC AAC TCT GTG AGG CTG CCG CCC TCT ATT

329
    Gln Ala Ile Pro Cys Ala Pro
1172 CAG GCC ATT CCT TGT GCA CCA TAG  TTTGGGTCTCTGACCCGTTCTTGCCC

1222 TCCTGAGTGAGTTAGGCCTTGGCATCATGGTGGCTGTGATACAAAAAAAGCTAGACTCC

1281 TGTGGGCCCCTTGACACATGGCAAAGCATAGTCCCACTGCAAACAGGGGACCATCCTCC
```

FIG. 4B

```
1340  TTGGGTCAGTGGGCTCTCAGGGCTTAGGAGGCAGAGTCTGAGTTTTCTGTGAGGTGAA
1399  GCTGGCCCTGACTCCTAGGAAGATGGATTGGGGGTCTGAGGTGTAAGGCAGAGGCCAT
1458  GGACAGGAGTCATCTTCTAGCTTTTAAAAGCCTTGTTGCATAGAGAGGGTCTTATCGC
1517  TGGGCTGGCCCTGAGGGGAATAGACCAGCGCCCACAGAAGAGCATAGCACTGGCCCTAG
1576  AGCTGGCTCTGTACTAGGAGACAATTGCACTAAATGAGTCCTATTCCCAAAGAACTGCT
1635  GCCCTTCCCAACCGAGCCCTGGGATGGTTCCCAAGCCAGTGAAATGTGAAGGGAAAAAA
1694  AATGGGTCCTGTGAAGGTTGGCTCCCCTTAGCCCTCAGAGGAATCTGCCTCACTACCTG
1753  CTCCAGCTGTGGGGCTCAGGAAAAAAAATGGCACTTTCTCTGTGGACTTTGCCACATT
1812  TCTGATCAGAGGTGTACACTAACATTTCTCCCCAGTCTAGGCCTTTGCAATTATTTATA
1871  TAGTGCCTTGCCTGGTGCCTGGCCCTCAGGCCTTGGCAGTCCTCAGCAGGCCCAG
1930  GGAAAAGGGGGTTGTGAGCGCCTTGAGCGCGTTGACTCTTGACTATCTATTAGAAACGCCAC
1989  CTAACTGCTAAATGGTGTTTGGTCATGTGGTGGACCTGTGTAAATATGTATATTTGTCT
2048  TTTTATAAAAATTTAAGTTGTTTACAAAAAAAAAA  2082
```

```
                 1                        25                         50
MOUSE    MPITRMRMRPWLEMQINSNQIPGLIWINKEEMIFQIPWKHAAKHGWDINK
         ++++  ++*x*****+*+***+*x***++*****++*x*  *************+*+*
HUMAN    MPITWMRMRPWLEMQINSNQIPGLIWINKEEMILEIPWKHAAKHGWDINK 75                        100
         DACLFRSWAIHTGRYKAGEKEPDPKTWKANFRCAMNSLPDIEEVKDQSRN
         ********+****+*******************+***********+*****
         DACLFRSWAIHTGRYKAGEKEPDPKTWKANFRCAMNSLPDIEEVKDQSRN 125                       150
         KGSSAVRVYRMLPPLTRNQRKERKSKSSRDTKSKTKRKLCGDVSPDTFSD
         ****+********  *+**+**********  *** *** *+***+**+
         KGSSAVRVYRMLPPLTKNQRKERKSKSSRDAKSKAKRLSCGDSSPDTFSD 175                       200
         GLSSSTLPDDHSSYTTQGYLGQDLDMERDITPALSPCVVSSSLSEWHMQM
         ***********+**   **   *-  *   ******  *** *   **
         GLSSSTLPDDHSSYTVPGYM-QDLEVEQALTPALSPCAVSSTLPDWHIPV 225                       250
         DIIPDSTTDLYNLQVSPMPSTSEAATDEDEEGKIAEDLMKLFEQSEWPQT
         r*** ****  ******  **+  *******  *** +*+*+****+*
         EVVPDSTSDLYNFQVSPMPSISEATTDEDEEGKLPEDIMKLLEQSEWQPT 275                       300
         HIDGKGYLLNEPGTQLSSVYGDFSCKEEPEIDSPRGDIGIGIQHVFTEMK
         +*+*****+*   *  **************+*+**     * *** *
         NVDGKGYLLNEPGVQPTSVYGDFSCKEEPEIDSPGGDIGLSLQRVFTDLK

329
         NMDSIMWMDSLLGNSVRLPPSIQAIPCAP
         **+  * **** ***+*+********
         NMDAT-WLDSLLTP-VRLP-SIQAIPCAP
```

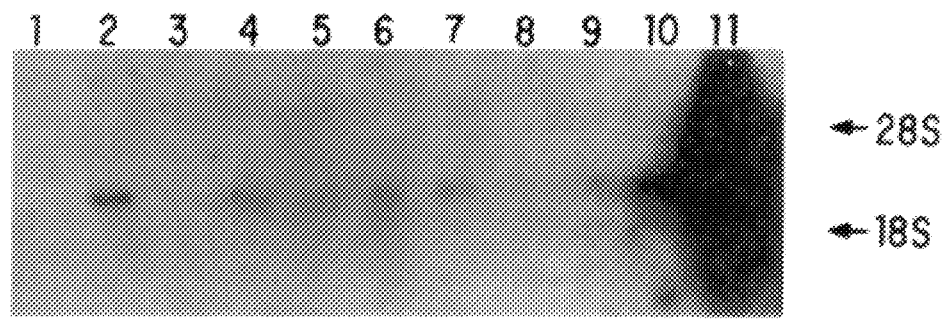
FIG.6A
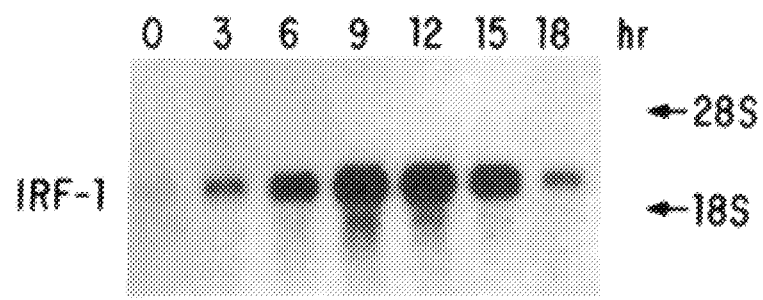
FIG.6B  IRF-1
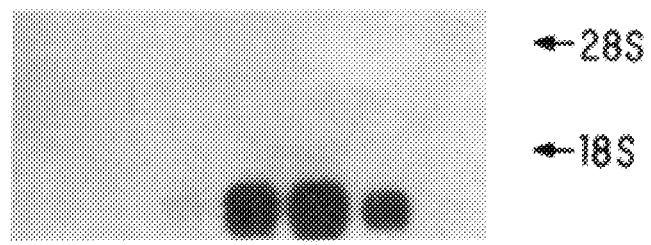
FIG.6C  IFN-β
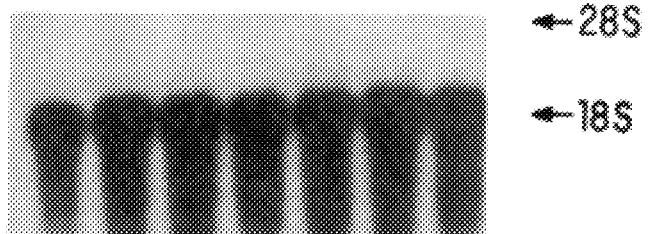
FIG.6D  β-Actin

FIG. 7A

```
         PstI
         CTGCAGAAAGAGGGGGACGGTCTCGGCTTTCCAAGACAGGCAAGGGGG
-299

GC Box 1              GC Box 2
CAGGGGAGTGGAGTGGAGCAAGGGGCGGGCCCGCGGTAGCCCCGGGGCGGTGGCGCGG
-251

GCCCGAGGGGGTGGGGAGCACAGCTGCCTTGTACTTCCCCTTCGCCGCTTAGCTCTAC
-193
                                         CAAT Box
AACAGCCTGATTTCCCCGAAATGATGAGGCCGAGTGGGCCAATGGGCGCGCAGGAGCG
-135

Minor Cap site
                                                      III
GCGCGGCGGGGGCGTGGCCGAGTCCGGGCCGGGGAATCCCGCTAAGTGTTTAGATTTC
-77                                                         -21

Major Cap site                              p1RF-L
               III
TTCGCGGCGCCGCGGACTCGCCAGTGCGCACCACTCCTTCGTCGAGGTAGGACGTGCT
-19                  +1

TTCACAGTCTAAGCCGAACCGAACCGAACCGAACCGAACCGAACCGGGCCGAGTTGCG
+39

CCGAGGTCAGCCGAGGTGGCCAGAGGACCCCAGCATCTCGGGCATCTTTCGCTTCGTG
+97

CGCGCATCGCGTACCTACACCGCAACTCCGTGCCTCGCTCTCCGGCACCCTCTGCGAA
+155
         PstI
TCGCTCCTGCAG
+213       +225
```

CGAGCCCCGCCGAACCGAGGCCACCCGGAGCCGTGCCCAGTCCACGC

CGGCCGTGCCCGGCGGCCTTAAGAACCAGGCAACCACTGCCTTCTTCCCT

CTTCCACTCGGAGTCGCGCTTCGCGCGCCCTCACTGCAGCCCCTGCGTCG

CCGGGACCCTCGCGCGCGACCAGCCGAATCGCTCCTGCAGCAGAGCCAAC

```
         10        20        30        40        50
ATGCCCATCACTTGGATGCGCATGAGACCCTGGCTAGAGATGCAGATTAA
MetProIleThrTrpMetArgMetArgProTrpLeuGluMetGlnIleAsn 60        70        80        90       100
TTCCAACCAAATCCCGGGGCTCATCTGGATTAATAAAGAGGAGATGATCT
 SerAsnGlnIleProGlyLeuIleTrpIleAsnLysGluGluMetIleLeu 110       120       130       140       150
TGGAGATCCCATGGAAGCATGCTGCCAAGCATGGCTGGGACATCAACAAG
 GluIleProTrpLysHisAlaAlaLysHisGlyTrpAspIleAsnLys 160       170       180       190       200
GATGCCTGTTTGTTCCGGAGCTGGGCCATTCACACAGGCCGATACAAAGC
 AspAlaCysLeuPheArgSerTrpAlaIleHisThrGlyArgTyrLysAla 210       220       230       240       250
AGGGGAAAAGGAGCCAGATCCCAAGACGTGGAAGGCCAACTTTCGCTGTG
 GlyGluLysGluProAspProLysThrTrpLysAlaAsnPheArgCysAla 260       270       280       290       300
CCATGAACTCCCTGCCAGATATCGAGGAGGTGAAAGACCAGAGCAGGAAC
 MetAsnSerLeuProAspIleGluGluValLysAspGlnSerArgAsn 310       320       340       340       350
AAGGGCAGCTCAGCTGTGCGAGTGTACCGGATGCTTCCACCTCTCACCAA
LysGlySerSerAlaValArgValTyrArgMetLeuProProLeuThrLys 360       370       380       390       400
GAACCAGAGAAAAGAAAGAAAGTCGAAGTCCAGCCGAGATGCTAAGAGCA
 AsnGlnArgLysGluArgLysSerLysSerSerArgAspAlaLysSerLys 410       420       430       440       450
AGGCCAAGAGGAAGTCATGTGGGGATTCCAGCCCTGATACCTTCTCTGAT
 AlaLysArgLysSerCysGlyAspSerSerProAspThrPheSerAsp 460       470       480       490       500
GGACTCAGCAGCTCCACTCTGCCTGATGACCACAGCAGCTACACAGTTCC
 GlyLeuSerSerSerThrLeuProAspAspHisSerSerTyrThrValPro
```

FIG. 8A

```
          510        520        530        540        550
     AGGCTACATGCAGGACTTGGAGGTGGAGCAGGCCCTGACTCCAGCACTGT
      GlyTyrMetGlnAspLeuGluValGluGlnAlaLeuThrProAlaLeuSer 560        570        580        590        600
     CGCCATGTGCTGTCAGCAGCACTCTCCCCGACTGGCACATCCCAGTGGAA
       ProCysAlaValSerSerThrLeuProAspTrpHisIleProValGlu 610        620        630        640        650
     GTTGTGCCGGACAGCACCAGTGATCTGTACAACTTCCAGGTGTCACCCAT
      ValValProAspSerThrSerAspLeuTyrAsnPheGlnValSerProMet 660        670        680        690        700
     GCCCTCCATCTCTGAAGCTACAACAGATGAGGATGAGGAAGGGAAATTAC
       ProSerIleSerGluAlaThrThrAspGluAspGluGluGlyLysLeuPro 710        720        730        740        750
     CTGAGGACATCATGAAGCTCTTGGAGCAGTCGGAGTGGCAGCCAACAAAC
       GluAspIleMetLysLeuLeuGluGlnSerGluTrpGlnProThrAsn 760        770        780        790        800
     GTGGATGGGAAGGGGTACCTACTCAATGAACCTGGAGTCCAGCCCACCTC
      ValAspGlyLysGlyTyrLeuLeuAsnGluProGlyValGlnProThrSer 810        820        830        840        850
     TGTCTATGGAGACTTTAGCTGTAAGGAGGAGCCAGAAATTGACAGCCCAG
       ValTyrGlyAspPheSerCysLysGluGluProGluIleAspSerProGly 860        870        880        890        900
     GGGGGGATATTGGGCTGAGTCTACAGCGTGTCTTCACAGATCTGAAGAAC
        GlyAspIleGlyLeuSerLeuGlnArgValPheThrAspLeuLysAsn 910        920        930        940        950
     ATGGATGCCACCTGGCTGGACAGCCTGCTGACCCCAGTCCGGTTGCCCTC
       MetAspAlaThrTrpLeuAspSerLeuLeuThrProValArgLeuProSer 960        970
     CATCCAGGCCATTCCCTGTGCACCGTAGCAGGGCCCCTGGGCCCCTCTTA
        IleGlnAlaIleProCysAlaPro***

TTCCTCTAGGCAAGCAGGACCTGGCATCATGGTGGATATGGTGCAGAGAA

GCTGGACTTCTGTGGGCCCCTCAACAGCCAAGTGTGACCCCACTGCCAAG

TGGGGATGGGCCTCCCTCCTTGGGTCATTGACCTCTCAGGGCCTGGCAGG

CCAGTGTCTGGGTTTTTCTTGTGGTGTAAAGCTGGCCCTGCCTCCTGGGA

AGATGAGGTTCTGAGACCAGTGTATCAGGTCAGGGACTTGGACAGGAGTC
```

FIG. 8B

AGTGTCTGGCTTTTCCTCTGAGCCTGCCCTGGAGAGGGTCTCGCTG
TCACTGGCTGGCTCCTAGGGGAACAGACCAGTGACCCCAGAAAGCATAA
CACCAATCCCAGGGCTGGCTCTGCACTAAGAGAAAATTGCACTAAATGAA
TCTCGTTCCAAAGAACTACCCCTTTTCAGCTGAGCCCTGGGACTGTTCC
AAAGCCAGTGAATGTGAAGGAAAGTGGGTCCTTCGGGCTCCTGGGACTGTTCC
CAGCCCTCAGAGGAGCTCTACCCTGCCTCCCCTGCTTTGGCTGAGGGCTTGG
GAAAAAACTTGGCACTTTTTCGTGTGGATCTTGCCACATTTCTGATCAG
AGGTGTACACTAACATTCCCCCGAGCTCTTGGCCTTTGCATTTATTTAT
ACAGTGCCCTTGCTCGGGGCCCACCACCCCTCAAGCCCCCAGCAGCCCTCA
ACAGGCCCAGGGAGGAAGTGTGAGCGCCTTGGTATGACTTAAAATTGGA
AATGTCATCTAACCATTAAGTCATGTGTGAACACATAAGGACGTGTGTAA
ATATGTACATTTGTCTTTTTATAAAAGTAAAATTGTT

FIG. 8C

FACTOR REGULATING GENE EXPRESSION

This application is a division of application Ser. No. 08/347,251, filed Nov. 18, 1994, (status: U.S. Pat. No. 5,616,698) which is a continuation of application Ser. No. 08/087,465, filed on Jul. 8, 1993, (status: abandoned), which is a continuation of application Ser. No. 07/397,967, filed Aug. 24, 1989, (now abandoned) originally entitled Factor Regulating Gene Expression.

FIELD OF THE INVENTION

The present invention relates generally to the regulation of gene expression. In particular the invention relates to a recombinant DNA molecule coding for a protein having the activity of an interferon regulatory factor-1 (IRF-1); to recombinant DNA molecules characterized by a DNA sequence coding for an IRF-1 active protein and a promoter and regulator sequence operably linked thereto; to the use of such DNA molecules for transforming host cells which are also transformed by DNA molecules coding for a desired protein and under the control of said IRF-1 active protein; to such DNA molecules including a sequence coding for a pharmaceutically active protein and a promoter region of the gene for said protein including a binding site for the IRF-1 active molecule; and to the production of said IRF-1 active protein and/or said pharmaceutically active protein by cultivation of suitable host cells transformed by said DNA molecules.

BACKGROUND OF THE INVENTION

Transcription of genes in mammalian cells is regulated by complex mechanisms wherein interactions of the regulatory DNA sequences with trans-acting DNA binding proteins play a central role. In the context of the regulation of transcription, genes encoding interferons (IFNs) represent a feature common to many of the cytokine genes; transcription of those genes is induced in a transient manner following various extra-cellular signals. It has been well documented that transcription of the genes for IFN-α and IFN-β is efficiently induced by viruses in a variety of cells, while that of the gene encoding IFN-γ is induced in T lymphocytes (T cells) following mitogenic stimulation (for a review see Weissmann and Weber, 1986; Taniguchi, 1938). IFN-β, a cytokine that was originally identified for its potent antiviral activity, also appears to play a crucial role in controlling cell growth and differentiation. In this regard, beside viruses and poly(rI):poly(rC) which are the well known inducers of IFN-β gene, many of the cytokines such as colony stimulating factor-1 (CSF-1) (Moore et al., 1984; Warren and Ralf, 1986; Resnitzky et al., 1986), tumor necrosis factor (TNF) (Onozaki et al., 1988), platelet-derived growth factor (PDGF) (Zullo et al., 1985) and IFNs (Kohase et al., 1987) also appear to induce IFN-β in certain cells, suggesting that they may transduce similar or identical signals in the target cells.

The IFN-β gene induction by viruses and poly(rI):poly (rC) has been shown to occur at the transcriptional level (Raji and Pitha, 1983; Ohno and Taniguchi, 1983; Dinter et al., 1983; Zinn et al., 1983). Thus cis-acting DNA sequences functioning as inducible enhancers have been identified within the 5'-flanking region of the human IFN-β gene (Fujita et al., 1985, 1987; Goodbourn et al., 1985; Dinter and Hauser, 1987). The inducible enhancer region (i.e. −65 to −105 with respect to the CAP site) contains repetitive hexanucleotide units some of which indeed function in the induced-activation of transcription when multimerized (Fujita et al., 1987). We have identified in mammalian cells such as mouse L929 cells and human cells, a factor, IRF-1, which specifically binds to the IFN-β regulatory sequences, as well as to the functional, repeated hexanucleotide sequences; (AAGTGA)$_4$. We have found that IRF-1 plays an essential role in virus-induced activation of IFN-β gene transcription by interacting with the identified cis-elements.

SUMMARY OF THE INVENTION

According to a broad aspect of this invention we provide a recombinant DNA molecule coding for a protein having the activity of an interferon regulatory factor-1 (IRF-1).

Preferably the DNA molecule codes for or is hybridizable to the DNA molecule coding for human IRF-1 or mouse (murine) IRF-1.

The DNA molecule is preferably one which codes for a protein which binds to the repeated oligomer sequence AAGTGA and the regulatory upstream elements of the human IFN-β-gene.

The DNA molecule may include a promoter region which is constitutive or inducible, for instance virus inducible e.g. by Newcastle Disease Virus or is inducible by mitogenic stimulation e.g. using Concanavalin A.

BRIEF DESCRIPTION OF THE FIGURES

FIGS. 4A–4C: The DNA and deduced protein sequence of the cDNA insert of pIRF-L.

FIG. 5: Comparison of the deduced amino acid sequences of murine and human IRF-1. The conserved amino acids are marked by asterisks. The sequences are presented with the one letter amino acid code as follows: A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; and Y, tyrosine.

FIG. 6: Expression of IRF-1 mRNA: (6A) Analysis of different tissues; (6B) Analysis as a function of time with IRF-1, IFN-β, and β-actin.

FIGS. 7A–7B: (7A) Nucleotide sequence of the PstI fragment from Ig14-2 which contains the mouse IRF-1 promoter sequence; (7B) Relative CAT activity.

FIG. 8: Nucleotide and deduced amino acid sequence of the human IRF-1 gene.

BRIEF DESCRIPTION OF THE PREFERRED EMBODIMENTS

Figure 1:
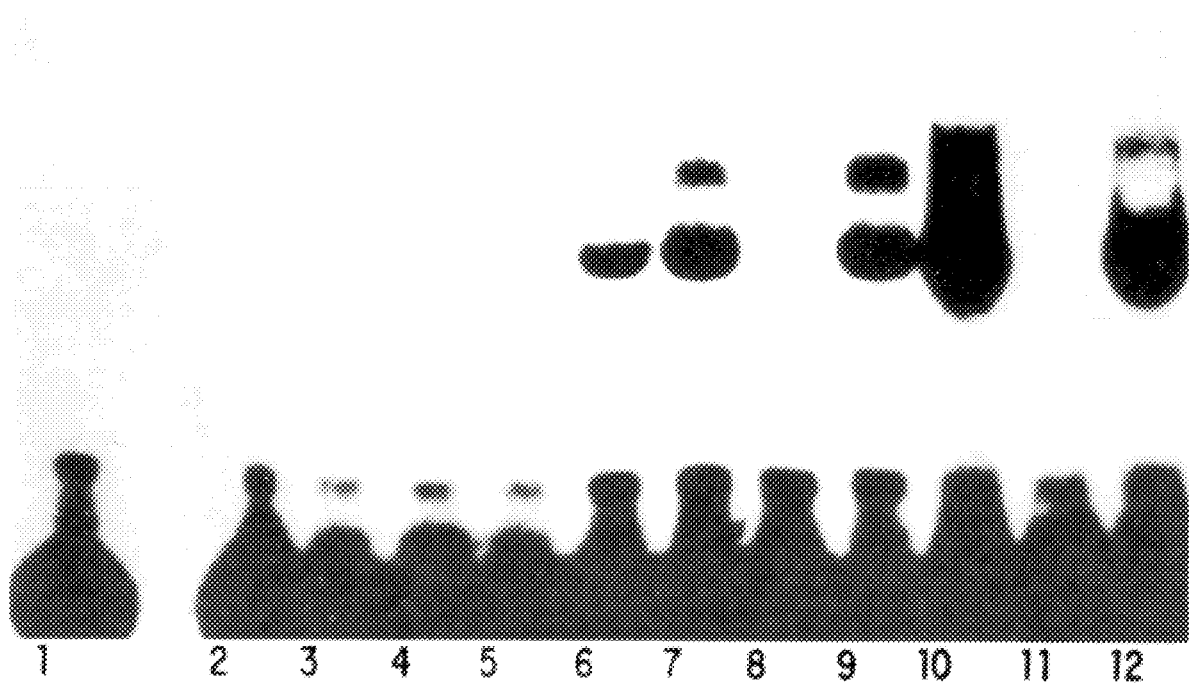
FIG. 1: Gel Retardation Assay.

One preferred DNA molecule (coding for human IRF-1) is characterised by a structural gene having the formula I below:

```
              10        20        30        40        50         Formula I
    ATGCCCATCACTTGGATGCGCATGAGACCCTGGCTAGAGATGCAGATTAA
              60        70        80        90       100
    TTCCAACCAAATCCCGGGGCTCATCTGGATTAATAAAGAGGAGATGATCT
             110       120       130       140       150
    TGGAGATCCCATGGAAGCATGCTGCCAAGCATGGCTGGGACATCAACAAG
             160       170       180       190       200
    GATGCCTGTTTGTTCCGGAGCTGGGCCATTCACACAGGCCGATACAAAGC
             210       220       230       240       250
    AGGGGAAAAGGAGCCAGATCCCAAGACGTGGAAGGCCAACTTTCGCTGTG
             260       270       280       290       300
    CCATGAACTCCCTGCCAGATATCGAGGAGGTGAAAGACCAGAGCAGGAAC
             310       320       340       340       350
    AAGGGCAGCTCAGCTGTGCGAGTGTACCGGATGCTTCCACCTCTCACCAA
             360       370       380       390       400
    GAACCAGAGAAAAGAAAGAAAGTCGAAGTCCAGCCGAGATGCTAAGAGCA
             410       420       430       440       450
    AGGCCAAGAGGAAGTCATGTGGGGATTCCAGCCCTGATACCTTCTCTGAT
             460       470       480       490       500
    GGACTCAGCAGCTCCACTCTGCCTGATGACCACAGCAGCTACACAGTTCC
             510       520       530       540       550
    AGGCTACATGCAGGACTTGGAGGTGGAGCAGGCCCTGACTCCAGCACTGT
             560       570       580       590       600
    CGCCATGTGCTGTCAGCAGCACTCTCCGCGACTGGCACATCCCAGTGGAA
             610       620       630       640       650
    GTTGTGCCGGACAGCACCAGTGATCTGTACAACTTCCAGGTGTCACCCAT
             660       670       680       690       700
    GCCCTCCATCTCTGAAGCTACAACAGATGAGGATGAGGAAGGGAAATTAC
             710       720       730       740       750
    CTGAGGACATCATGAGGCTCTTGGAGCAGTCGGAGTGGCAGCCAACAAAC
             760       770       780       790       800
    GTGGATGGGAAGGGGTACCTACTCAATGAACCTGGAGTCCAGCCCACCTC
             810       820       830       840       850
    TGTCTATGGAGACTTTAGCTGTAAGGAGGAGCCAGAAATTGACAGCCCAG
             860       870       880       890       900
    GGGGGGATATTGGGCTGAGTCTACAGCGTGTCTTCACAGATCTGAAGAAC
             910       920       930       940       950
    ATGGATGCCACCTGGCTGGACAGCCTGCTGACCCCAGTCCGGTTGCCCTC
             960       970
    CATCCAGGCCATTCCCTGTGCACCG
``` or a dengenerate variant thereof.

The DNA molecule may for example be characterized by a structural gene having the formula defined above and upstream and downstream flanking sequences contained within the following formula II:

```
CGAGCCCCGCCGAACCGAGGCCACCCGGAGCCGTGCCCAGTCCACGC    Formula II

CGGCCGTGCCCGGCGGCCTTAAGAACCAGGCAACCACTGCCTTCTTCCCT
```

-continued

```
CTTCCACTCGGAGTCGCGCTTCGCGCGCCCTCACTGCAGCCCCTGCGTCG

CCGGGACCCTCGCGCGCGACCAGCCGAATCGCTCCTGCAGCAGAGCCAAC 10        20        30        40        50
ATGCCCATCACTTGGATGCGCATGAGACCCTGGCTAGAGATGCAGATTAA
          60        70        80        90       100
TTCCAACCAAATCCCGGGGCTCATCTGGATTAATAAAGAGGAGATGATCT
         110       120       130       140       150
TGGAGATCCCATGGAAGCATGCTGCCAAGCATGGCTGGGACATCAACAAG
         160       170       180       190       200
GATGCCTGTTTGTTCCGGAGCTGGGCCATTCACACAGGCCGATACAAAGC
         210       220       230       240       250
AGGGGAAAAGGAGCCAGATCCCAAGACGTGGAAGGCCAACTTTCGCTGTG
         260       270       280       290       300
CCATGAACTCCCTGCCAGATATCGAGGAGGTGAAAGACCAGAGCAGGAAC
         310       320       340       340       350
AAGGGCAGCTCAGCTGTGCGAGTGTACCGGATGCTTCCACCTCTCACCAA
         360       370       380       390       400
GAACCAGAGAAAAGAAAGAAAGTCGAAGTCCAGCCGACATGCTAAGAGCA
         410       420       430       440       450
AGGCCAAGAGGAAGTCATGTGGGGATTCCAGCCCTGATACCTTCTCTGAT
         460       470       480       490       500
GGACTCAGCAGCTCCACTCTGCCTGATGACCACAGCAGCTACACAGTTCC
         510       520       530       540       550
AGGCTACATGCAGGACTTGGAGGTGGAGCAGGCCCTGACTCCAGCACTGT
         560       570       580       590       600
CGCCATGTGCTGTCAGCAGCACTCTCCCCGACTGGCACATCCCAGTGGAA
         610       620       630       640       650
GTTGTGCCGGACAGCACCAGTGATCTGTACAACTTCCAGGTGTCACCCAT
         660       670       680       690       700
GCCCTCCATCTCTGAAGCTACAACAGATGAGGATGAGGAAGGGAAATTAC
         710       720       730       740       750
CTGAGGACATCATGAAGCTCTTGGAGCAGTCGGAGTGGCAGCCAACAAAC
         760       770       780       790       800
GTGGATGGGAAGGGGTACCTACTCAATGAACCTGGAGTCCAGCCCACCTC
         810       820       830       840       850
TGTCTATGGAGACTTTAGCTGTAAGGAGGAGCCAGAAATTGACAGCCCAG
         860       870       880       890       900
GGGGGGATATTGGGCTGAGTCTACAGCGTGTCTTCACAGATCTGAAGAAC
         910       920       930       940       950
ATGGATGCCACCTGGCTGGACAGCCTGCTGACCCCAGTCCGGTTGCCCTC
         960       970
CATCCAGGCCATTCCCTGTGCACCGTAGCAGGGCCCCTGGGCCCCTCTTA

TTCCTCTAGGCAAGCAGGACCTGGCATCATGGTGGATATGGTGCAGAGAA

GCTGGACTTCTGTGGGCCCCTCAACAGCCAAGTGTGACCCCACTGCCAAG

TGGGGATGGGCCTCCCTCCTTGGGTCATTGACCTCTCAGGGCCTGGCAGG

CCAGTGTCTGGGTTTTTCTTGTGGTGTAAAGCTGGCCCTGCCTCCTGGGA

AGATGAGGTTCTGAGACCAGTGTATCAGGTCAGGGACTTGGACAGGAGTC

AGTGTCTGGCTTTTTCCTCTGAGCCCAGCTGCCTGGAGAGGGTCTCGCTG
```

-continued
TCACTGGCTGGCTCCTAGGGGAACAGACCAGTGACCCCAGAAAAGCATAA

CACCAATCCCAGGGCTGGCTCTGCACTAAGAGAAAATTGCACTAAATGAA

TCTCGTTCCAAAGAACTACCCCTTTTCAGCTGAGCCCTGGGGACTGTTCC

AAAGCCAGTGAATGTGAAGGAAAGTGGGGTCCTTCGGGGCAATGCTCCCT

CAGCCTCAGAGGAGCTCTACCCTGCTCCCTGCTTTGGCTGAGGGGCTTGG

GAAAAAAACTTGGCACTTTTTCGTGTGGATCTTGCCACATTTCTGATCAG

AGGTGTACACTAACATTTCCCCCGAGCTCTTGGCCTTTGCATTTATTTAT

ACAGTGCCTTGCTCGGGGCCCACCACCCCCTCAAGCCCCAGCAGCCCTCA

ACAGGCCCAGGGAGGGAAGTGTGAGCGCCTTGGTATGACTTAAAATTGGA

AATGTCATCTAACCATTAAGTCATGTGTGAACACATAAGGACGTGTGTAA

ATATGTACATTTGTCTTTTTATAAAAAGTAAAATTGTT or a degenerate variant thereof.

Another preferred DNA molecule (coding for murine IRF-1) is characterized by a structural gene having the following formula III:

```
ATG CCA ATC ACT CGA ATG CGG ATG AGA CCC TGG CTA GAG ATG CAG ATT    Formula III
AAT TCC AAC CAA ATC CCA GGG CTG ATC TGG ATC AAT AAA GAA GAG ATG
ATC TTC CAG ATT CCA TGG AAG CAC GCT GCT AAG CAC GGC TGG GAC ATC
AAC AAG GAT GCC TGT CTG TTC CGG AGC TGG GCC ATT CAC ACA GGC CGA
TAC AAA GCA GGA GAA AAA GAG CCA GAT CCC AAG ACA TGG AAG GCA AAC
TTG CGT TGT GCC ATG AAC TCC CTG CCA GAC ATC GAG GAA GTG AAG GAT
CAG AGT AGG AAC AAG GGC AGC TCT GCT GTG CGG GTG TAC CGG ATG CTG
CCA CCC CTC ACC AGG AAC CAG AGG AAA GAG AGA AAG TCC AAG TCC AGC
CGA GAC ACT AAG AGC AAA ACC AAG AGG AAG CTG TGT GGA GAT GTT AGC
CCG GAC ACT TTC TCT GAT GGA CTC AGC AGC TCT ACC CTA CCT GAT GAC
CAC AGC AGT TAC ACC ACT CAG GGC TAC CTG GGT CAG GAC TTG GAT ATG
GAA AGG GAC ATA ACT CCA GCA CTG TCA CCG TGT GTC GTC AGC AGC AGT
CTC TCT GAG TGG CAT ATG CAG ATG GAC ATT ATA CCA GAT AGC ACC ACT
GAT CTG TAT AAC CTA CAG GTG TCA CCC ATG CCT TCC ACC TCC GAA GCC
GCA ACA GAC GAG GAT GAG GAA GGG AAG ATA GCC GAA GAC CTT ATG AAG
CTC TTT GAA CAG TCT GAG TGG CAG CCG ACA CAC ATC GAT GGC AAG GGA
TAC TTG CTC AAT GAG CCA GGG ACC CAG CTC TCT TCT GTC TAT GGA GAC
TTC AGC TGC AAA GAG GAA CCA GAG ATT GAC AGC CCT CGA GGG GAC ATT
GGG ATA GGC ATA CAA CAT GTC TTC ACG GAG ATG AAG AAT ATG GAC TCC
ATC ATG TGG ATG GAC AGC CTG CTG GGC AAC TCT GTG AGG CTG CCG CCC
TCT ATT CAG GCC ATT CCT TGT GCA CCA TAG
``` or a degenerate variant thereof.

Such a DNA molecule as mentioned in the foregoing paragraph may, for example, be characterized by a structural gene having the formula defined above and upstream and downstream flanking sequences contained within the following formula IV:

```
   1 GGACGTGCTTTCACAGTCTAAGCCGAACCGAACCGAACCGAACCGAACCGAACCGGGCC     Formula IV
  60 GAGTTGCGCCGAGGTCAGCCGAGGTGGCCAGAGGACCCCAGCATCTCGGGCATCTTTCG
 119 CTTCGTGCGCGCATCGCGTACCTACACCGCAACTCCGTGCCTCGCTCTCCGGCACCCTC 178 TGCGAATCGCTCCTGCAGCAA    AGCCACC ATG CCA ATC ACT CGA ATG CGG
 227 ATG AGA CCC TGG CTA GAG ATG CAG ATT AAT TCC AAC CAA ATC CCA
 272 GGG CTG ATC TGG ATC AAT AAA GAA GAG ATG ATC TTC CAG ATT CCA
 317 TGG AAG CAC GCT GCT AAG CAC GGC TGG GAC ATC AAC AAG GAT GCC
 362 TGT CTG TTC CGG AGC TGG GCC ATT CAC ACA GGC CGA TAC AAA GCA
 407 GGA GAA AAA GAG CCA GAT CCC AAG ACA TGG AAG GCA AAC TTC CGT
 452 TGT GCC ATG AAC TCC CTG CCA GAC ATC GAG GAA GTG AAG GAT CAG
 497 AGT AGG AAC AAG GGC AGC TCT GCT GTG CCG GTG TAC CGG ATG CTG
 542 CCA CCC CTC ACC AGG AAC CAG AGG AAA GAG AGA AAG TCC AAG TCC
 587 AGC CGA GAC ACT AAG AGC AAA ACC AAG AGG AAG CTG TGT GGA GAT
 632 GTT AGC CCG GAC ACT TTC TCT GAT GGA CTC AGC AGC TCT ACC CTA
 677 CCT GAT GAC CAC AGC AGT TAC ACC ACT CAG GGC TAC CTG GGT CAG
 722 GAC TTG GAT ATG GAA AGG GAC ATA ACT CCA GCA CTG TCA CCG TGT
 767 GTC GTC AGC AGC AGT CTC TCT GAG TGG CAT ATG CAG ATG GAC ATT
 812 ATA CCA GAT AGC ACC ACT GAT CTG TAT AAC CTA CAG GTG TCA CCC
 857 ATG CCT TCC ACC TCC GAA GCC GCA ACA GAC GAG GAT GAG GAA GGG
 902 AAG ATA GCC GAA GAC CTT ATG AAG CTC TTT GAA CAG TCT GAG TGG
 947 CAG CCG ACA CAC ATC GAT GCC AAG GGA TAC TTG CTC AAT GAG CCA
 992 GGG ACC CAG CTC TCT TCT GTC TAT GGA GAC TTC AGC TGC AAA GAG
1037 GAA CCA GAG ATT GAC AGC CCT CGA GGG GAC ATT GGG ATA GGC ATA
1082 CAA CAT GTC TTC ACG GAG ATG AAG AAT ATG GAC TCC ATC ATG TGG
1127 ATG GAC AGC CTG CTG GGC AAC TCT GTG AGG CTG CCG CCC TCT ATT
1172 CAG GCC ATT CCT TGT GCA CCA TAG    TTTGGGTCTCTGACCCGTTCTTGCCC
1222 TCCTGAGTGAGTTAGGCCTTGGCATCATGGTGGCTGTGATACAAAAAAAGCTAGACTCC
1281 TGTGGGCCCCTTGACACATGGCAAAGCATAGTCCCACTGCAAACAGGGGACCATCCTCC
1340 TTGGGTCAGTGGGCTCTCAGGGCTTAGGAGGCAGAGTCTGAGTTTTCTTGTGAGGTGAA
1399 GCTGGCCCTGACTCCTAGGAAGATGGATTGGGGGGTCTGAGGTGTAAGGCAGAGGCCAT
1458 GGACAGGAGTCATCTTCTAGCTTTTTAAAAGCCTTGTTGCATAGAGAGGGTCTTATCGC
1517 TGGGCTGGCCCTGAGGGGAATAGACCAGCGCCCACAGAAGAGCATAGCACTGGCCCTAG
1576 AGCTGGCTCTGTACTAGGAGACAATTGCACTAAATGAGTCCTATTCCCAAAGAACTGCT
1635 GCCCTTCCCAACCGAGCCCTGGGATGGTTCCCAAGCCAGTGAAATGTGAAGGGAAAAAA
1694 AATGGGGTCCTGTGAAGGTTGGCTCCCTTAGCCTCAGAGGGAATCTGCCTCACTACCTG
1753 CTCCAGCTGTGGGGCTCAGGAAAAAAAAATGGCACTTTCTCTGTGGACTTTGCCACATT
1812 TCTGATCAGAGGTGTACACTAACATTTCTCCCCAGTCTAGGCCTTTGCATTTATTTATA
1871 TAGTGCCTTGCCTGGTGCCTGCTGTCTCCTCAGGCCTTGGCAGTCCTCAGCAGGCCCAG
1930 GGAAAAGGGGGGTTGTGAGCGCCTTGGCGTGACTCTTGACTATCTATTAGAAACGCCAC
1989 CTAACTGCTAAATGGTGTTTGGTCATGTGGTGGACCTGTGTAAATATGTATATTTGTCT
2048 TTTTATAAAAATTTAAGTTGTTTACAAAAAAAAAA 2082
``` or a degenerate variant thereof.

DNA sequences of the invention coding for proteins having IRF-1 activity include DNA sequences from a eukaryotic source such as, not only human and mouse but also, e.g. chicken, frog and yeast, which hybridize with the DNA sequences of the foregoing human or murine IRF-1 (FIGS. I to IV) and which code for a protein having IRF-1 activity.

One such cDNA molecule which hybridize to the cDNA of murine IRF-1 as defined in FIG. 4A (and is named IRF-2) is set forth below in formula IIIa:

```
              10           20           30           40           Formula IIIa
         ATGCCGGTGGAACGGATGCGAATGCGCCCGTGGCTGGAGGAGCAG 50           60           70           80           90
         ATAAATTCCAATACGATACCAGGGCTAAAGTGGCTGAACAAGGAG 100          110          120          130
              AAGAAGATTTTCCAGATCCCCTGGATGCATGCGGCTCGGCACGGA 140          150          160          170          180
              TGGGACGTGGAAAAGGATGCTCCGCTCTTCAGAAACTGGGCGATC 190          200          210          220
              CATACAGGAAAGCATCAACCAGGAATAGATAAACCAGATCCAAAA 230          240          250          260          270
              ACATGGAAAGCAAATTTTCGATGTGCCATGAATTCCCTGCCCGAC
```

-continued

```
          280            290            300            310
ATT GAG GAA GT GAA GGA CAG AAG CAT AAA GAA AGG AAA CAA CGC C 320            330            340            350            360
TT CAG AGT CT ACC GGA TGC TGC CCT TAT CCG AAC GAC CTT CCA AG 370            380            390            400
AAA GGA AAG AAA CC AAA GAC AGA AAA AGA AGA GAG AGT TAA GCA C 410            420            430            440            450
AT CAA GCA AGA ACC AGT TGA GTC ATC TTT GGG GCT TAG TAA TGG A 460            470            480            490
GT AAG TGG CTT TTC TCC TGA GTA TGC GGT CCT GAC TTC AGC TAT A 500            510            520            530            540
AAA AAT GAA GTG GAT AGT ACG GTG AAC ATC ATA GTT GTA GGA CAG 550            560            570            580
TCC CAT CTG GAC AGC AAC ATT GAA GAT CAA GAG ATC GTC ACT AAC 590            600            610            620            630
CCG CCA GAC ATC TGC CAG GTT GTA GAA GTG ACC ACT GAG AGT GAT 640            650            660            670
GAC CAG CCA GTC AGC ATG AGT GAG CT CTA CCC TCT ACA GAT TTC T 680            690            700            710            720
CCT GTG TCT TCC TAC GCA GAA AGC GAA ACT ACC GAC AGT GTG GCC 730            740            750            760
AGT GAT GAA GAG AAC GCA GAG GGG AGA CCA CAC TGG AGG AAG AGG 770            780            790            800            810
AGC ATC GAA GGC AAG CAG TAC CTC AGC AAC ATG GGG ACA CGG AAC 820            830            840            850
ACC TAT CTG CTG CCC AGC ATG GCG ACC TTT GTC ACC TCC AAC AAG 860            870            880            890            900
CC AGA TCT GCA GGT CAC CAR CAA AGA GGA TAG CTG TCC GAT GCC T 910            920            930            940
TAC AAC AGC TCC TGG CCC CCA TTT ACA GAC CTT CCC CTT CCT GCC 950            960            970            980            990
CC AGT GAC CCC CAC GCC CAG CAG CAG TCG GCC AGA CCG GGA GAC C 1000           1010           1020           1030
CGG GCC AGT GTC ATC AAG AAG ACA TCT GAT ATC ACC CAG GCC CGT

1040
GTC AAG AGC TGT
``` or is a degenerate variant thereof.

This DNA molecule may, for example be characterized by a structural gene having the formula defined above and upstream and downstream flanking sequences contained within the following formula IVa:

```
                                             TCT CAG GCA AGC CGG GGA

CT AAC TTT TAG TTT TGC TCC TGC GAT TAT TCA ACT GAC GGG CTT T

CAT TTC CAT TTT ACA CAC CCT AAC AAC ACT CAC ACC TTG CGG GAT

TGT ATT GGT AGC GTG GAA AAA AAA AAA GCA CAT TGA GAG GGT ACC 10             20             30             40
ATG CCG GTG GAA CGG ATG CGA ATG CGC CCG TGG CTG GAG GAG CAG 50             60             70             80             90
ATA AAT TCC AAT ACG ATA CCA GGG CTA AAG TGG CTG AAC AAG GAG 100            110            120            130
AAG AAG ATT TTC CAG ATC CCC TGG ATG CAT GCG GCT CGG CAC GGA
```

-continued

```
         140          150          160          170          180
TGGGACGTGGAAAAGGATGCTCCGCTCTTCAGAAACTGGGCGATC 190          200          210          220
CATACAGGAAAGCATCAACCAGGAATAGATAAACCAGATCCAAAA 230          240          250          260          270
ACATGGAAAGCAAATTTTCGATGTGCCATGAATTCCCTGCCCGAC 280          290          300          310
ATTGAGGAAGTGAAGGACAGAAGCATAAAGAAAGGAAACAACGCC 320          330          340          350          360
TTCAGAGTCTACCGGATGCTGCCCTTATCCGAACGACCTTCCAAG 370          380          390          400
AAAGGAAAGAAACCAAAGACAGAAAAAGAAGAGAGTTAAGCAC 410          420          430          440          450
ATCAAGCAAGAACCAGTTGAGTCATCTTTGGGGCTTAGTAATGGA 460          470          480          490
GTAAGTGGCTTTTCTCCTGATGTAGCGGTCCTGACTTCAGCTATA
         500          510          520          530          540
AAAAATGAAGTGGATAGTACGGTGAACATCATAGTTGTAGGACAG
              550          560          570          580
TCCCATCTGGACAGCAACATTGAAGATCAAGAGATCGTCACTAAC
         590          600          610          620          630
CCGCCAGACATCTGCCAGGTTGTAGAAGTGACCACTGAGAGTGAT
              640          650          660          670
GACCAGCCAGTCAGCATGAGTGAGCTCTACCCTCTACAGATTTCT
         680          690          700          710          720
CCTGTGTCTTCCTACGCAGAAAAGCGAAACTACCGACAGTGTGGCC
              730          740          750          760
AGTGATGAAGAGAACGCAGAGGGGAGACCACACTGGAGGAAGAGG
         770          780          790          800          810
AGCATCGAAGGCAAGCAGTACCTCAGCAACATGGGGACACGGAAC
              820          830          840          850
ACCTATCTGCTGCCCAGCATGGCGACCTTTGTCACCTCCAACAAG
         860          870          880          890          900
CCAGATCTGCAGGTCACCATCAAAGAGGATAGCTGTCCGATGCCT
              910          920          930          940
TACAACAGCTCCTGGCCCCCATTTACAGACCTTCCCCTTCCTGCC
         950          960          970          980          990
CCAGTGACCCCCACGCCCAGCAGCAGTCGGCCAGACCGGGAGACC
              1000         1010         1020         1030
CGGGCCAGTGTCATCAAGAAGACATCTGATATCACCCAGGCCCGT

1040
GTCAAGAGCTGTTAAGCCTTTGACTCTCCCTGGTGGTTGTTGGGA

TTTCTTAGCTTTGTGTTGTTCTTTGTTTGTATTATATTATTTTTT

TTCTCTATGATACCTATCTTAGACACATCTAAGGGAGAAAGCCTT

GACGATAGATTATTGATTGCTGTGTCCAACTCCAGAGCTGGAGCT

TCTTCTTAACTCAGGACTCCAGCCCCCCCCCCCCTCGGTAGATG

CGTATCTCTAGAACCTGCTGGATCTGCCAGGGCTACTCCCTCAAG

TTCAAGGACCAACAGCCACACGGGCAGTGGAGGTGCTGCGTTGCC

TACGGTCAAGGCCAGCATGGTGGAGTGGATGCCTCAGAACGGAGG

AGAAAATGTGAACTAGCTGGAATTTTTTATTCTTGTGAATATGT

ACATAGGGCAGTACGAGCAATGTCGCGGGCTGCTTCTGCACCTTA

TCTTGAAGCACTTACAATAGGCCTTCTTGTAATCTTGCTCTCCTT
CACAGCACACTCGGCGACCCCTTCTGTGTCCACTACCCCACTACC
```

-continued
```
CACCCCTCCCTCCTCAACCCCTCCATCCCGGTCCTCTATGCGCCC

CTTCCCCCCAACCAATCCCATCACAACCTCTTACCTATCCTTTCC

CTCCCAACCCCTTCTATCCCAGCCCACCACCTACCCCACTCCTCC

CCAACTCCTCCATTCTAGCCCATTACCCACGCCTCTCTCCTCAGC

CCAGCCTACCCCATCCCACCCTGTTCCTTTCCTCCAGTTTCCTCT

CCTCAAAGGCAAGGCTCTACATCTTGGAGGAGGAGGAGGAGAAGA

AAATGAGTTTCTTCACCGCTGTCCCATTTTAAGACTGCTTGAATA

ATAAAAAAAAATCTTTCTAATCTGCTATGCTTGAATGGCACGCGG

TACAAAGGAAAACTGTCATGGAAATATTATGCAAATTCCCAGATC

TGAAGACGGAAAATACTCTAATTCTAACCAGAGCAAGCTTTTTA

TTTTTTTATACAAGGGGAATATTTTATTCAAGGTAAAAAAATTCT

AAATAAAATATAATTGTTTTTTATCTTTTCTACAGCAAATTTATA

ATTTTAAGATTCCTTTTCCTGTTCATCAGCAGTTGTTATTACATC

CCTTGTGGCACATTTTTTTTTAATTTGTAAAGGTGAAAAAAAA

ACTTTTATGAGCTCATGTAGCAATCAAATTATCCTGTGGATTGAT

AATAAATGAATATGGTATATAGTTAAAGATTTTAAAAAAAAAAAA
``` or a degenerate variant thereof.

We describe below the isolation of cDNA molecules from human cells and mouse cells coding for human and murine IRF-1 and from mouse cells and yeast which hybridize respectively to the cDNA of murine IRF-1 and human IRF-1.

The recombinant DNA molecule may also contain a promoter and regulatory sequence contained within the following formula V:

Formula V

```
            PstI
        CTGCAG AAAGAGGGGGACGGTCTCGGCTTTCCAAGACAGGCAAGGGGG
        -299

GC Box 1                          GC Box 2
        CAGGGGAGTGGAGTGGAGCAA GGGGCGG GCCCGCGGTAGCCCC GGGGCGG TGGCGCGG
        -251

GCCCGAGGGGGTGGGGAGCACAGCTGCCTTGTACTTCCCCTTCGCCGCTTAGCTCTAC
        -193

CAAT Box
        AACAGCCTGATTTCCCCGAAATGATGAGGCCGAGTG GGCCAAT GGGCGCGCAGGAGCG
        -135

Minor Cap site
        GCGCGGCGGGGGCGTGGCCGAGTCCGGGCCGGGGAATCCCGCTAAGTGTTTAGATTTTC
        -77                                                           -21
```

-continued

```
                 Major Cap site                                    ┌─p1RF—L
                      ▼▼▼
    TTCGCGGCGCCGCGGACTCGCCAGTGCGCACCACTCCTTCGTCGAGGTAGGACGTGCT
    -19                     +1

TTCACAGTCTAAGCCGAACCGAACCGAACCGAACCGAACCGGGCCGAGTTGCG
    +39

CCGAGGTCAGCCGAGGTGGCCAGAGGACCCCAGCATCTCGGGCATCTTTCGCTTCGTG
    +97

CGCGCATCGCGTACCTACACCGCAACTCCGTGCCTCGCTCTCCGGCACCCTCTGCGAA
    +155

PstI
    TCGCTCCTGCAG
    +213      +225
``` or a degenerate variant thereof.

The recombinant DNA molecule may also be designed for expression of a pharmaceutically active protein such as e.g. a cytokine or a plasminogen activator and in this form will contain preferably a structural gene for a desired pharmaceutically active protein operably linked to a promoter region of the gene for the said protein including a binding site for the IRF-1 active molecule.

Thus a recombinant DNA molecule of the invention may comprise a DNA sequence as defined above and a structural gene for a desired pharmaceutically active protein under the control of the IRF-1 active protein coded for by said DNA sequence. In such a recombinant DNA molecule the gene coding for the IRF-1 active molecule is preferably under the control of a constitutive promoter or most preferably an inducible promoter. Preferably the gene for the desired pharmaceutically active protein will include an IRF binding site containing repetitive AAGTGA sequences.

The present invention also comprehends a host cell e.g. a bacterial cell e.g. E. coli, or a yeast cell or a mammalian cell e.g. a CHO cell or a mouse cell e.g. L929, transformed by a recombinant DNA molecule as defined above. Ideally the host cell will be selected from a cell line which has no or substantially no level of endogenous IRF-1 activity.

Alternatively for the production of a pharmaceutically active protein a host cell may be transformed by a first DNA molecule containing a sequence coding for a protein having the activity of an IRS-1, and by a second separate DNA molecule containing a gene coding for a desired, pharmaceutically active protein that is under the control of the IRF-1 active protein that is coded for by the first DNA molecule. Preferably the first DNA molecule coding for the IRF-1 active molecule includes a constitutive promoter or most preferably an inducible promoter sequence operably linked to the gene coding for the IRF-1 active compound. Also, preferably the second DNA molecule includes a binding site for the IRF-1 active protein containing repetitive AAGTGA sequences.

The IRF-1 active protein or the pharmaceutically active protein can be produced by cultivation of the transformed cell and isolation of the produced protein in conventional manner.

Suitably the host cells are induced by treatment in a manner appropriate to the promoter which is operably linked to the gene coding for the IRF-1, as discussed below.

The invention also comprehends a protein having the activity of an IRF-1 obtained by the cultivation of a host transformed with a DNA molecule as defined above.

A preferred protein having the activity of an IRF-1 has the formula VI:

| Formula VI | | | | | | | | | | | | | | | |
|---|---|---|---|---|---|---|---|---|---|---|---|---|---|---|---|
| Met | Pro | Ile | Thr | Arg | Met | Arg | Met | Arg | Pro | Trp | Leu | Glu | Met | Gln | Ile |
| Asn | Ser | Asn | Gln | Ile | Pro | Gly | Leu | Ile | Trp | Ile | Asn | Lys | Glu | Glu | Met |
| Ile | Phe | Gln | Ile | Pro | Trp | Lys | His | Ala | Ala | Lys | His | Gly | Trp | Asp | Ile |
| Asn | Lys | Asp | Ala | Cys | Leu | Phe | Arg | Ser | Trp | Ala | Ile | His | Thr | Gly | Arg |
| Tyr | Lys | Ala | Gly | Glu | Lys | Glu | Pro | Asp | Pro | Lys | Thr | Trp | Lys | Ala | Asn |
| Phe | Arg | Cys | Ala | Met | Asn | Ser | Leu | Pro | Asp | Ale | Glu | Glu | Val | Lys | Asp |
| Gln | Ser | Arg | Asn | Lys | Gly | Ser | Ser | Ala | Val | Arg | Val | Tyr | Arg | Met | Leu |
| Pro | Pro | Leu | Thr | Arg | Asn | Gln | Arg | Lys | Glu | Arg | Lys | Ser | Lys | Ser | Ser |
| Arg | Asp | Thr | Lys | Ser | Lys | Thr | Lys | Arg | Lys | Leu | Cys | Gly | Asp | Val | Ser |
| Pro | Asp | Thr | Phe | Ser | Asp | Gly | Leu | Ser | Ser | Ser | Thr | Leu | Pro | Asp | Asp |
| His | Ser | Ser | Tyr | Thr | Thr | Gln | Gly | Tyr | Leu | Gly | Gln | Asp | Leu | Asp | Met |
| Glu | Arg | Asp | Ile | Thr | Pro | Ala | Leu | Ser | Pro | Cys | Val | Val | Ser | Ser | Ser |
| Leu | Ser | Glu | Trp | His | Met | Gln | Met | Asp | Ile | Ile | Pro | Asp | Ser | Thr | Thr |
| Asp | Leu | Tyr | Asn | Leu | GlN | Val | Ser | Pro | Met | Pro | Ser | Thr | Ser | Glu | Ala |
| Ala | Thr | Asp | Glu | Asp | Glu | Glu | Gly | Lys | Ile | Ala | Glu | Asp | Leu | Met | Lys |
| Leu | Phe | Glu | Gln | Ser | Glu | Trp | Gln | Pro | Thr | His | Ile | Asp | Gly | Lys | Gly |
| Tyr | Leu | Leu | Asn | Glu | Pro | Gly | Thr | GlN | Leu | Ser | Ser | Val | Tyr | Gly | Asp |
| Phe | Ser | Cys | Lys | Glu | Glu | Pro | Glu | Ile | Asp | Ser | Pro | Arg | Gly | Asp | Ile |
| Gly | Ile | Gly | Ile | Gln | His | Val | Phe | Thr | Glu | Met | Lys | Asn | Met | Asp | Ser |
| Ile | Met | Trp | Met | Asp | Ser | Leu | Leu | Gly | Asn | Ser | Val | Arg | Leu | Pro | Pro |
| Ser | Ile | Gln | Ala | Ile | Pro | Cys | Ala | Pro | | | | | | | |

Another preferred protein having the activity of an IRF-1 has the formula VII:

Formula II
MetProIleThrTrpMetArgMetArgProTrpLeuGluMet

GlnIleAsnSerAsnGlnIleProGlyLeuIleTrpIleAsnLysGluGluMetIleLeu

GluIleProTrpLysHisAlaAlaLysHisGlyTrpAspIleAsnLysAspAlaCysLeu

PheArgSerTrpAlaIleHisThrGlyArgTyrLysAlaGlyGluLysGluProAspPro

LysThrTrpLysAlaAsnPheArgCysAlaMetAsnSerLeuProAspIleGluGluVal

LysAspGlnSerArgAsnLysGlySerSerAlaValArgValTryArgMetLeuProPro

LeuThrLysAsnGlnArgLysGluArgLysSerLysSerSerArgAspAlaLysSerLys

AlaLysArgLysSerCysGlyAspSerSerProAspThrPheSerAspGlyLeuSerSer

SerThrLeuProAspAspHisSerSerTyrThrValProGlyTyrMetGlnAspLeuGlu

ValGluGlnAlaLeuThrProAlaLeuSerProCysAlaValSerSerThrLeuProAsp

TrpHisIleProValGluValValProAspSerThrSerAspLeuTyrAsnPheGlnVal

SerProMetProSerIleSerGluAlaThrThrAspGluAspGluGluGlyLysLeuPro

GluAspIleMetLysLeuLeuGluGlnSerGluTrpGlnProThrAsnValAspGlyLys

GlyTryLeuLeuAsnGluProGlyValGlnProThrSerValTyrGlyAspPheSerCys

LysGluGluProGluIleAspSerProGlyGlyAspIleGlyLeuSerLeuGlnArgVal

PheThrAspLeuLysAsnMetAspAlaThrTrpLeuAspSerLeuLeuThrProValArg

LeuProSerIleGlnAlaIleProCysAlaPro

Yet another preferred protein (IRF-2), which is coded for by the cDNA sequence of formula IIIa has the formula VIII:

Formula VIII

MetProValGluArgMetArgMetArgProTrpLeuGluGluGln

IleAsnSerAsnThrIleProGlyLeuLysTrpLeuAsnLysGlu

LysLysIlePheGlnIleProTrpMetHisAlaAlaArgHisGly

TrpAspValGluLysAspAlaProLeuPheArgAsnTrpAlaIle

HisThrGlyLysHisGlnProGlyIleAspLysProAspProLys

ThrTrpLysAlaAsnPheArgCysAlaMetAsnSerLeuProAsp

IleGluGluValLysAspArgSerIleLysLysGlyAsnAsnAla

PheArgValTyrArgMetLeuProLeuSerGluArgProSerLys

LysGlyLysLysProLysThrGluLysGluGluArgValLysHis

IleLysGlnGluProValGluSerSerLeuGlyLeuSerAsnGly

ValSerGlyPheSerProGluTyrAlaValLeuThrSerAlaIle

LysAsnGluValAspSerThrValAsnIleIleValValGlyGln

SerHisLeuAspSerAsnIleGluAspGlnGluIleValThrAsn

ProProAspIleCysGlnValValGluValThrThrGluSerAsp

AspGlnProValSerMetSerGluLeuTyrProLeuGlnIleSer

ProValSerSerTyrAlaGluSerGluThrThrAspSerValAla

SerAspGluGluAsnAlaGluGlyArgProHisTrpArgLysArg

SerIleGluGlyLysGlnTyrLeuSerAsnMetGlyThrArgAsn

ThrTyrLeuLeuProSerMetAlaThrPheValThrSerAsnLys

-continued
ProAspLeuGlnValThrIleLysGluAspSerCysProMetPro

TyrAsnSerSerTrpProProPheThrAspLeuProLeuProAla

ProValThrProThrProSerSerSerArgProAspArgGluThr

ArgAlaSerValIleLysLysThrSerAspIleThrGlnAlaArg

ValLysSerCys

We describe below the molecular cloning and characterization of murine and human cDNA encoding DNA binding proteins having the IRF-1 activity.

A remarkable sequence conservation will be seen between the murine and human IRF-1 molecules, as revealed from the analysis of the cloned cDNAs. Furthermore, expression of the gene encoding IRF-1 is shown to be induced by Newcastle Disease Virus (NDV) and Concanavalin A (ConA) in mouse L929 cells and splenic lymphocytes, respectively As used herein, a "functional derivative" is a compound which possesses a biological activity (either functional or structural) that is substantially similar to a biological activity of IFR-1. The term "functional derivative" is intended to include the "fragments," "variants," "analogues," or "chemical derivatives" of a molecule. A "fragment" of a molecule such as IFR-1, is meant to refer to any polypeptide subset of the molecule. A "variant" of a molecule such as IFR-1 is meant to refer to a molecule substantially similar in structure and function to either the entire molecule, or to a fragment thereof. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules is not found in the other, or if the sequence of amino acid residues is not identical.

EXAMPLES

1. Cloning and expression of IRF-1 DNA in *E. coli*

A. Poly(A)$^+$ RNA was isolated from uninduced mouse L929 cells and used to synthesis cDNA (following the procedure of Aruffo and Seed, 1987). The resulting cDNA was then cloned into an EcoRI-cleaved λgt11 vector and a cDNA library constructed according to the standard procedure of Huynh et al., 1985, using *E. coli* Y1090 as the host strain.

The resulting λgt11 library was then screened using the multimerized (4 times) AAGTGA sequence (hereinafter referred to as the C1 oligomer; Fujita et al., 1987) as the probe.

In this screening procedure *E. coli* Y1090, infected by the recombinant λgt11 phages was plated onto 10×13 cm square plates. The plates were then incubated at 12° C. for 4 to 5 hours when about 20,000 plaques/plate were visible.

Membrane filters for screening were either nylon (Nytran; Schleicher & Schnell) or nitrocellulose (Schleicher & Schnell) membranes. The filters were immersed in 10 mM IPTG (Isopropyl-b-D-thiogalactopyranoside for the induction of lacZ gene expression in the appropriate phage plaques) and air dried, then overlayed on the plates and incubated at 37° C. for 2.5 hours. Plaques will only produce a protein encoded by cDNA if the cDNA is in-frame with the lacZ gene.

The filters were then removed and chilled at 4° C. for 20 minutes and, without drying, were subjected to screening.

The membrane filters were then prepared for assay as follows:

Nuclear extract was prepared from mouse L929 cells and it was spotted (in an amount corresponding to about 10 μg protein) onto the membranes.

Prior to effecting DNA binding a Binding Buffer consisting of 10 mM Hepes, pH 7.5, 5.0 mM NaCl, 1 mM DTT, 1 mM EDTA, 5% glycerol was used. 5% of non-fat powder milk (Yukijurishi Inc.) was added to the buffer and the filters were incubated in the mixture for 1 hour at 4° C. and then rinsed for 1 minute in the same buffer but containing no powder milk.

The filters were then incubated in binding buffer (1 ml) containing 350 μg/ml of salmon sperm DNA of average length of approximately 300 bp and $^{32}$P-labelled probe C1 oligomer DNA ($10^6$ cpm/ml; specific activity 2,000 cpm/f mole) (see Fujita et al., 1987). The probe DNA was end labeled at the 5'-termini [γ-$^{32}$P]ATP using T4 kinase.

After the binding, the filters were washed at room temperature with the Binding Buffer for 1 to 2 hours (10 ml filter) changing the Binding buffer several times during this operation. The filters were then air-dried and subjected to autoradiography. In this assay the nylon membranes, but not the nitrocellulose membranes, gave a positive signal which was specifically inhibited by including excess unlabeled C1 oligomer.

About $1.4 \times 10^6$ recombinants were screened in this way. Among the 32 positive phage clones identified in the first screening, one clone (designated λL28-8) was found to bind repeatedly with the probe DNA in subsequent rounds of screening.

2. Production and Purification of protein in transfected *E. coli*

Lysogenic bacterial clones were prepared by transfecting *E.coli* Y1089 with λL28-8. Overnight lysogens harboring λL28-8 were then seeded at 1% in 400 ml L-Broth. The bacteria were grown at 31° C. until the $OD_{600}$ became 1. The temperature was then shifted to 42° C. for 20 min. IPTG was then added to 10 mM and, after incubating at 38° C. for a further 20 min. the cultures were rapidly pelleted and suspended in 10 ml of Lysis Buffer which consists of 20 mM Hepes pH 7.9, 0.2 mM EDTA, 0.5 mM spermidine, 0.15 mM spermine, 0.1 mM DTT, 10% glycerol, 0.5 mM phenylmethyonylsulphonylfluoride (PMSF), 1 μg/ml pepstatin A, 1 μg/ml leupeptine, 500 μM L-I-tosylamide-2-phenylethylchloromethylbenzamidine, 10 mM sodium molybdate, 2 mM sodium pyrophosphate and 2 mM sodium orthovanadate. Cell suspensions were subjected to three rapid freeze-thaw cycles and subsequently centrifuged at 30,000 rpm for 1 hr. at 4° C. using a Beckman 50 Ti rotor. The supernatant was used either directly for a gel retardation assay (see below) or was further purified.

Further purification was carried out as follows:

Approximately 4 ml of the supernatant was applied on poly(di-C): poly(di-C)-column with a bed volume of 2 ml, and equilibrated with Lysis Buffer. The flow-through material (4 ml) was then applied on a DE 52 (Whatman) column having a bed volume of 2 ml equilibrated with Buffer Z (25 mM Hepes, pH 7.8, 12.5 mM $MgCl_2$, 1 mM DTT, 20% glycerol, 0.1% NP-40 (NONIDET™ P-40, an octylphenol-ethylene oxide condensate having an average of 9 moles ethylene oxide per mole of phenol), 0.5 mM PMSF). The DNA binding activity was eluted by Buffer Z containing 0.1M KCl. The eluate (approximately 4 ml) was further concentrated using centricon-10 (Amicon). The final protein concentration was 28 mg/ml.

3. Characterisation of the Protein Product of the Clone λL28-8:

(1) Gel retardation assay

Lysogenic bacterial clones harbouring λL28-8 were prepared by transfecting *E. coli* Y1089 and were induced to express the cloned cDNA at high levels using the procedure of Huynh et al., 1985. Lysogenic clones prepared and treated in the same manner with the phage lacking the cDNA insert (designated λ6) were used as a control.

Extracts each containing 3 μg protein were prepared from the induced cultures of the Lysogen (four preparations designated λL28-8a, λL28-8b and λ6a and λ6b).

Nuclear extract (3 λg protein) was also prepared from mouse L929 cells.

The extracts were incubated with 1 fmole labeled C1 oligomer probe as described above having a specific activity of 8,000 cpm/fmole.

Each extract was also subject to competitive assay in which a competitor DNA was added at various concentrations to the incubation.

The results of the assay are shown in FIG. 1 in which the various lanes correspond to the following:

| Lane | Extract |
|------|---------|
| 1 | none |
| 2 | λ6a |
| 3 | λ6b |
| 4 | λ6b with 1,000 fold molar excess of unlabeled C1 oligomer |
| 5 | λb with 1,000 fold molar excess of unlabeled C5A oligomer* |
| 6 | λL28-8a |
| 7 | λL28-8b |
| 8 | λL28-8b with 1,000 fold molar excess of unlabeled C1 oligomer |
| 9 | L28-8b with 1,000 fold molar excess of unlabeled C5A oligomer* |
| 10 | L929 cell |
| 11 | L929 cell with 1,000 fold molar excess of unlabeled C1 oligomer |
| 12 | L929 cell with 1,000 fold molar excess of unlabeled C5A oligomer* |

*The C5A oligomer is described in Fujita et al., 1985, and is a 6 times repeated GAAA sequence.

From FIG. 1 it will be apparent that bound probes are detectable in lanes 6, 7, 9, 10 and 12.

As shown in FIG. 1 protein extracts from the λL28-8 lysogens gave rise to shifted bands (lanes 6 and 7), the appearance of which was inhibited by excess unlabeled C1 oligomer DNA but not by the same amount of the C5A oligomer (lanes 8 and 9).

In contrast to λL28-8-derived proteins those prepared from the induced λ6-derived lysogens failed to give such shifted bands (lanes 2–5). The shifted bands can be seen to be closely similar to those of the natural IRF-1 from mouse L929 cells (lanes 10 and 12). Such differences as exist in the two sets of shifted bands is considered to be a consequence of the different amounts of protein bound to the probe DNA.

In addition, it is found that the shifted bands were detectable only with the proteins from IPTG-induced Y1089 cells transfected with λL28-8.

(ii) DNAase Footprinting analysis

Footprinting analysis was carried out to test the binding properties of the protein encoded by λL28-8 cDNA to a DNA encoding the IFN-β gene upstream region.

Protein encoded by λL28-8 cDNA was extracted from the induced lysogen and partially purified by column chromatography as described above and tested for its binding properties to a DNA containing the IFN-β gene upstream region.

Probe DNAs were prepared as SalI-HindIII fragments isolated from p-125cat (containing the wild type IFN-β gene) and p-125DPcat (containing a mutant IFN-β gene). The plasmid p-125cat was constructed as p-105cat (Fujita et al., 1987), except the BamHI (−125)-TagI (+19) fragment from pSE-125 (Fujita et al., Cell, Vol. 41, pp 489–496, 1985) was used. Plasmid p-125DPcat, carrying point mutations within the IFN-β regulatory elements were obtained by synthetic oligo nucleotide directed mutagenesis on p-125cat as described in Hatakeyama et al., Proc. Natl. Acad. Sci. U.S.A., Vol. 83, pp 9650–9654, 1986). Both DNAs were labeled at the HindIII site by [$\gamma$-$^{32}$P]ATP using T4 kinase.

4 fmoles of the probe DNA (specific activity 3,000 cpm/fmole) was incubated in the 20 $\mu$l reaction mixture containing 25 mM Tris-HCl, pH 7.9, 6.25 mM MgCl$_2$, 50 mM KCl, 1 mM EDTA, 0.5 mM DTT, 10% glycerol, 2% polyvinylalcohol in the presence or absence of 280 $\mu$g of the purified protein.

In the assay 5×10$^{-4}$ unit of DNAase I (Worthington) was added and incubated for 1 min. at 25° C.

Figure 2:
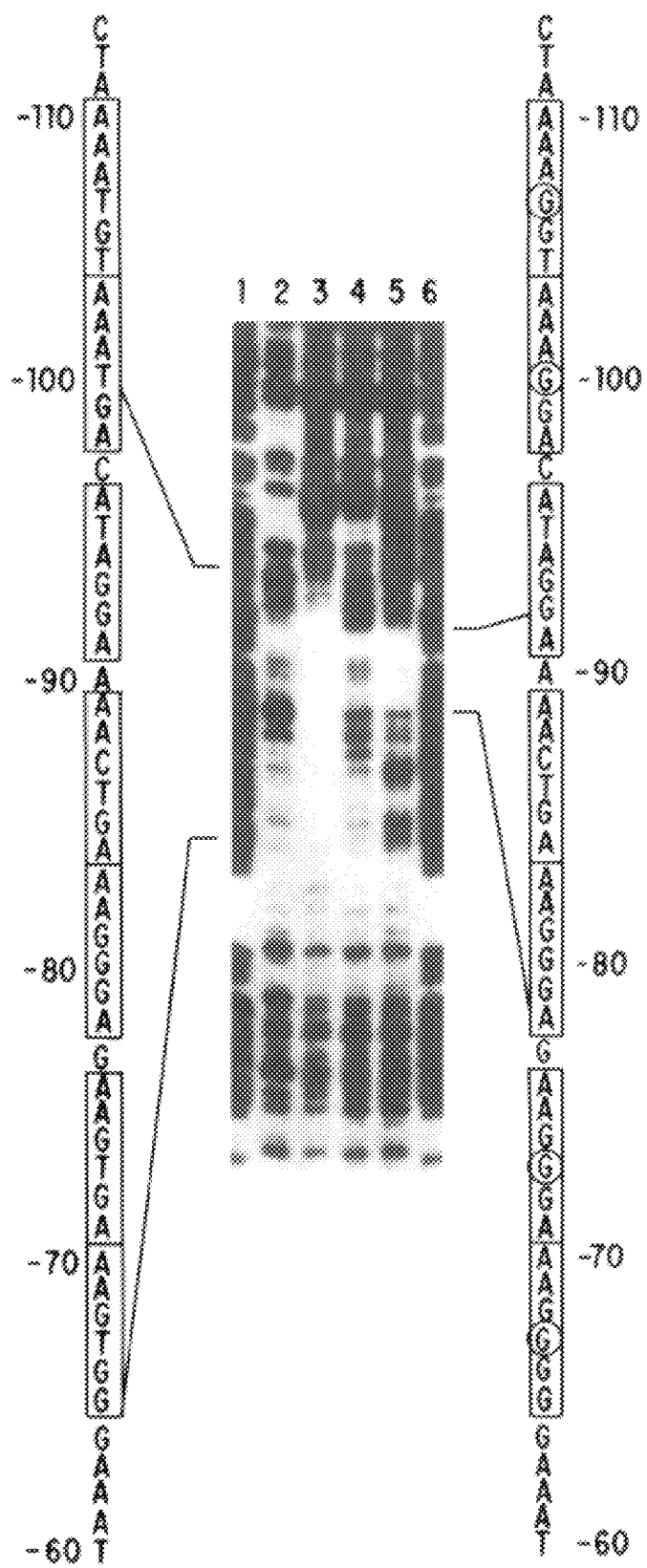
FIG. 2: DNAase Footprinting Analysis. The sequence on the left side of FIG. 2 is part of a DNA sequence of the wild type IFN-β probe. The DNA sequence on the right side of FIG. 2 is part of the DNA sequence of the mutant IFN-β probe.

FIG. 2 shows autoradiograms of the DNA fragments obtained from samples obtained by carrying out the following procedures. On the left hand side of FIG. 2 is part of the DNA sequence of the wild type IFN-β probe, and on the right hand side of FIG. 2 is part of the DNA sequence of the mutant IFN-β probe.

1. The wild type IFN-β probe was cleaved by A+G reactions (see Methods in Enzymology, Vol. 65, pp 499–560)—result shown in lane 1.
2. The wild type IFN-β probe was partially digested by DNAase I without protection—result shown in lane 2.
3. The wild type IFN-β probe was reacted with the protein and then digested with DNAase I—result shown in lane 3.
4. The wild type IFN-β probe was reacted with the protein in the presence of 1,000 fold molar excess of unlabeled C1 oligomer and then digested with DNAase I—result shown in lane 4.
5. The mutant IFN-β probe was reacted with the protein and then digested by DNAase I—result shown in lane 5.
6. The mutant IFN-β probe was cleaved by A+G reactions—result shown in lane 6.

In FIG. 2 the protected regions as revealed in lanes 3 and 5 are indicated respectively on the sequences depicted on the left and right sides of the autoradiogram. The hexamer motifs are framed.

From the results in FIG. 2 it will be seen that the protected region corresponds to nucleotides −100 to −64, this being the region found to be protected by IRF-1 obtained from L929 cells. The protection was abrogated by the use of excess unlabeled C1 oligomer (lane 4). It was also found, using lower protein concentrations, that preferential protection occurred in the region containing the AAGTGA motif (−80 to −70).

These results indicate that the protein has a higher affinity to the region containing the AAGTGA motif and a lower affinity to the surrounding region.

The mutant IFN-β gene segment carries T- G mutations at positions −106, −100, −73 and −67. In comparing lanes 5 and 2, under the same assay conditions the protection afforded by the recombinant proteins appears restricted to the unmutated region (lane 2). This observation is in conformity with the observation that the introduction of these mutations results in a dramatic reduction (20 fold) of the inducibility of transcription by NDV in L929 cells and that in vitro binding of IRF-1 to the mutant IFN-β gene was notable only in the unmutated region.

Further, the use of the C1 oligomer reveals that the protein specifically protects the region containing the oligomer sequences. This protection corresponded identically to that afforded by native IRF-1 derived from L929 cells.

3. DNA Competition Assay

This assay was carried out to examine the affinity of the recombinant protein to various DNA sequences including some of the known transcriptional regulatory DNA sequences. The procedure was as follows:

The HindIII-SalI fragment of IFN-β probe was isolated from p-125 cat (see Fijita et al., 1987); this fragment contains the human IFN-β gene sequence from +19 to −125. The DNA was labeled at the 3' termini by filling in both ends with [$\alpha$-$^{32}$P] dCTP using Klenow fragment.

The specific activity of the probe DNA was 8,000 cpm/fmole.

The gel retardation assays were carried out under the conditions described above.

Figure 3C:
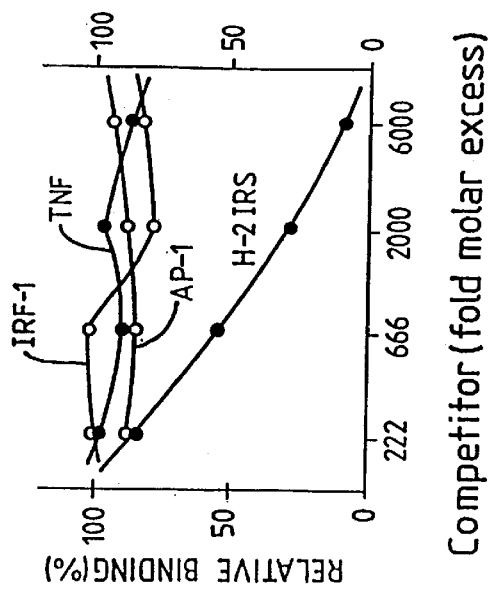
FIG. 3: DNA Competition Assay: the left hand panel shows the results obtained when the hexamers were used as competitor; the middle panel gives the results when human EFN gene segments were used as competitors; the right hand panel gives the results when the various DNA segments as indicated within the panel were used.
Figure 3B:
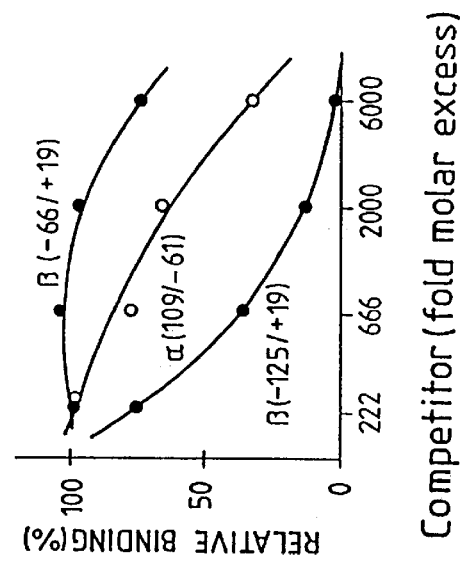
Figure 3A:
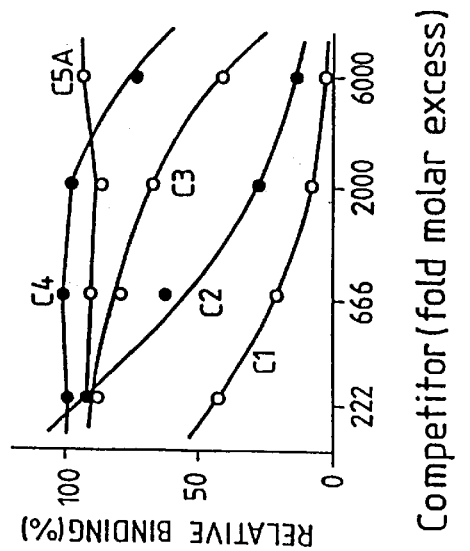

In the competition assay runs the DNA was reacted with the protein in the presence of various concentrations of competitor DNAs in the binding mixture as indicated in FIG. 3.

The formation level of the complex was quantitated by densitometric analysis of the autoradiogram. Complex formation in the absence of competitor DNA was taken to be 100%.

The structure of the competitor DNAs were as follows:

a) AP-1: a synthetic DNA having the following sequence

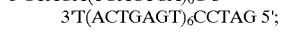

5'CTAGA(TGACTCA)$_6$G 3'
       3'T(ACTGAGT)$_6$CCTAG 5';

b) TNF: 37 bp of synthetic DNA that encompasses from +1162 to +2116 (see Nedwin et al., 1985) of the TNF-α first intron;

c) murine H2-D$^d$: 37 bp of synthetic DNA that encompasses the IRS element (−159 to −123) as described by Korber et al., 1988;

d) human IFN-α: 46 bp synthetic DNA corresponding to virus Response Element, see Ryals et al., 1985.

e) Hexamer sequences C1, C2, C3, C4 and C5A. The sequences C1 and C5A are as described above. Sequences C2, C3 and C4 are as published in Cell, 49, 352–367 (1987); they represent the sequences
AAATGA—C2
AAGGGA—C3 and
AAAGGA—C4 respectively f) the IFN-β gene sequence from +19 to −66.

In FIG. 3 the left hand panel shows the results obtained when the hexamer repeats were used as competitors. The middle panel gives the results when human IFN gene segments were used as competitors, and the right hand panel gives the corresponding results, using various DNA segments as indicated within the panel.

From the results shown in FIG. 3 it will be seen that the appearance of the shifted band was competed out by the hexamer sequences in order of efficiency C1- C2- C3- C4, but was not competed out significantly by C5A.

It can also be observed that the synthetic DNA segment encompassing the regulatory elements of either human IFN-α1 or murine H-2D$^d$ genes gave rise to a competitive activity. This is particularly interesting as the DNA segment of the H-2D$^d$ gene contains the so-called IFN-response sequence (IRS) that functions as an enhancer when the cells respond to IFN (Sugita et al., 1987; Israel et al., 1986; Korber et al., 1988).

In fact, sequence motifs similar or identical to these found on the IFN-β gene are found in many of the promoter sequences of the IFN-inducible genes where nuclear factors appear to bind specifically (Korber et al., 1988; Lery et al., 1988).

The results given in FIG. 3 are closely similar to those obtained when the assay is repeated under similar conditions using natural protein produced from L929 cells.

Structure of the CDNA encoding murine IRF-1

The DNA sequence of the cloned DNAs was determined either by a dideoxy method (SEQUENASE; United States Biochemical, Inc.) or by the standard Maxam-Gilbert method (Maxam and Gilbert, 1980).

The λL28-8 insert in E.coli Y1089 was isolated as follows: the phage DNA was prepared by standard procedure and the DNA was digested by EcoRI then the cDNA cleaved out of the phage DNA was isolated and sequenced by the dideoxy method (Sequenase: United States Biochemical Inc.). The cDNA insert in λL28-8 was found to be 1.8 kb long. The nucleotide sequence analysis revealed a large open reading frame linked in phase with the β-galactoside gene.

To screen clones containing larger cDNA inserts, double stranded cDNA was synthesised with L929 cell derived poly(A)$^+$RNA and cloned into vector CDM8 according to the published procedure of Aruffo and Seed (Prod. Natl. Acad. Sci., U.S.A., Vol 84, pp 8573, 1987) and Seed (Nature, Vol. 329, pp. 840–842, 1987).

The recombinant plasmids were introduced into E.coli strain MC1061/p3 (according to the procedure of Aruffo and Seed; as above) and the clones of cDNA were screened using the λL28-8-derived ($^{32}$p-labeled) cDNA probe under low stringent conditions for DNA-DNA hybridization (Kashima et al, Nature, Vol. 313, pp 402–404, 1985), and a clone pIRF-L was selected for further study.

The desired cDNA insert of pIRF-L was obtained by digestion with HindIII and XbaI and sequenced by the methods described above. The sequence is shown in Formula IV and in FIG. 4.

The cDNA sequence from λL28-8 was found to contain an identical sequence in the overlapping region except that one A residue was missing between nucleotides 1773 and 1781.

Figure 4D:
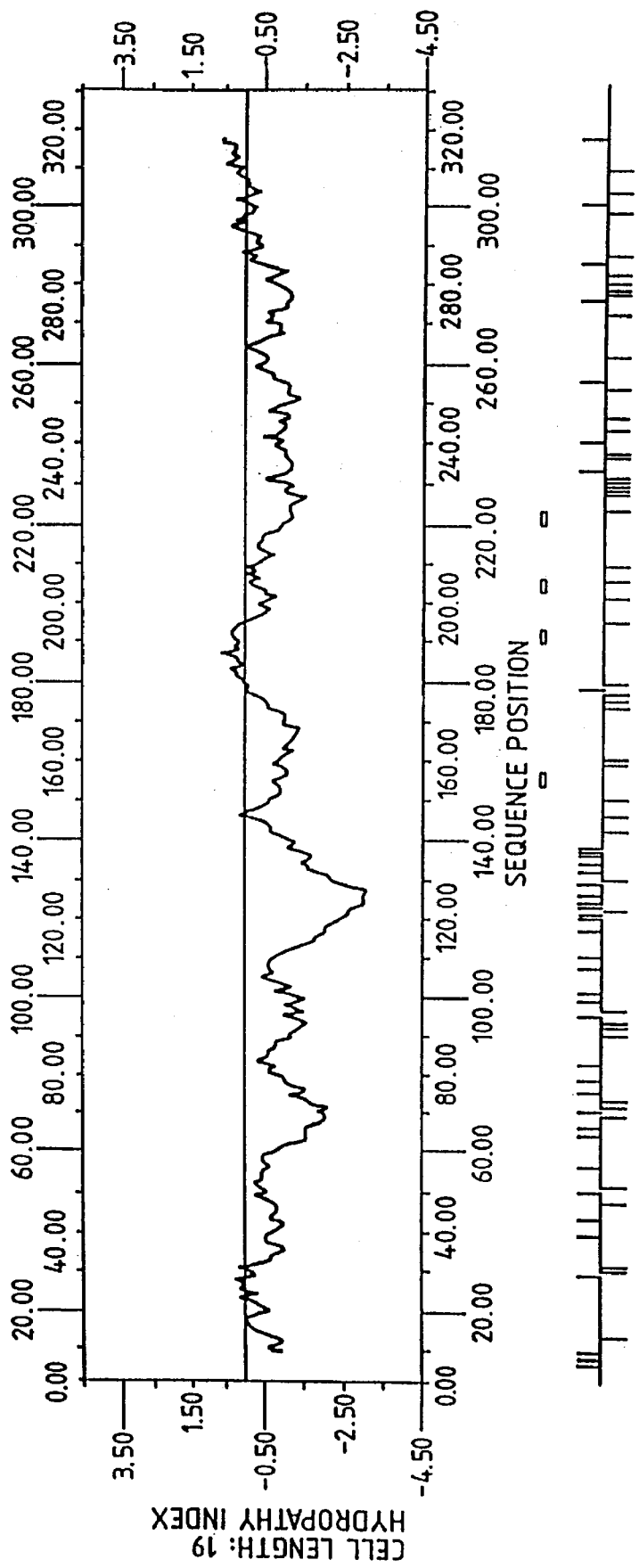
FIG. 4D: Hydropathy plot analysis.

The 5' and 3' termini of the λL28-8 derived CDNA are marked by arrows in FIG. 4. The ATTTATTTA and ATTTA sequences which possibly confer the mRNA instability are framed.

As will be apparent from FIG. 4A the cDNA of the murine cDNA derived from pIRF-L was 198 bp and 20 bp longer than that of the λL28-8 cDNA in the 5'and 3' regions, respectively.

Analysis of the genomic DNA sequence containing the promoter region of this gene reveals that the cDNA of pIRF-L is missing about 30 bp from the major CAP site, see below and Formula V and FIG. 7.

The immediate upstream sequence of the first ATG codon, GGACCATGC, fits well with Kozak's consensus sequence GCC$_G^A$CCATGG, for the translation initation site.

An in-frame ATG sequence was not found in the upstream sequence from the above mentioned ATG sequence confirming that it is indeed the initiation codon for the IRF-1 mRNA.

As mentioned above, no difference in nucleotide sequence was detected between the cDNAs of λL28-8 and pIRF-L within the overlapping regions, except one nucleotide in the 3'-non-coding region.

The murine IRF-1 was thus found to consist of 329 amino acids with a calculated M.W. of 37.3 KD. Canonical N-glycosylation sites do not appear within the sequence.

No significant homology to other known proteins was detected by searching in Protein Sequence Database (Natl. Biomed. Res. Found., Washington, D.C.) and more recently published sequences.

Hydropathy plot analysis according to Kyte and Doolittle, 1982, indicates that the protein as a whole is highly hydrophilic (FIG. 4B).

Inspection of the deduced primary sequence of the murine IRF-1 reveals the following features:

The amino terminal half, extending to amino acid (a.a.) 140 is rich in lysin (Lys) and arginine (Arg). In fact 31 out of 39 of the total Lys and Arg residues are located in this region. In the lower panel of FIG. 4B is represented a diagrammatic summary of the location of the basic amino acids (Arg, Lys) (upward columns) and acidic amino acids (Asp, Glu) (downward columns).

As shown in FIG. 4B, this region shows strong hydrophilicity and is considered to be the region primarily responsible for the binding of IRF-1 to the specific DNA sequences.

In this connection, characteristic motifs for many DNA binding proteins such as Zinc fingers and helix-turn-helix motifs (Pabo and Sauer, 1984, Evans and Hollenberg, 1988) were not detectable in the IRF-1 protein.

In contrast the rest of the molecule (i.e. the carboxyl terminal half) shows a relative abundance of aspartic acid (Asp), glutamic acid (Glu), Serine (Ser) and Threonine (Thr). Of 189 amino acids (from a.a. 140 to 329), 33 (17%) represent acidic amino acids and 36 (19%) represent Ser and Thr. Notably at cluster of 5 consecutive acidic amino acids is found in a.a. 227 to 231. With regard to Ser and Thr, many appear to form clusters (region at a.a. 153–156, 190–192, 206–208, 220–222; referred to as the S-T regions herein). The S-T regions are depicted by small open rectangles in the lower panel of FIG. 4B.

Structure of the cDNA encoding human IRF-1

Following a procedure similar to that described above for the murine IRF-1, human IRF-1 cDNA was cloned and sequenced.

A human CDNA library was prepared by synthesising cDNA using poly(A)$^+$RNA from a human T cell line Jurkat. The double stranded CDNA synthesis and subsequent cloning into plasmid vector CDM8 was carried out according to the procedure of Aruffo and Seed (Proc. Natl., Acad. Sci., U.S.A., Vol. 84, pp 8573–8577, 1987) and Seed (Nature, Vol. 329, pp 840–842, 1987).

The recombinant plasmids were introduced into E.coli strain, MC1061/p3 using the procedure of Aruffo and Seed as mentioned above.

Clones of cDNA that cross-hybridize with mouse IRF-I cDNA were screened using λL28-8 cDNA ($^{32}$p-labeled) as the probe under low stringent conditions for DNA-DNA hybridization. The conditions employed were exactly as described by Kashima et al. (Nature, Vol. 313, pp 402–404, 1985). Hybridization was performed at 65° C. for 20 hours in a medium containing 1M NaCl, 50 mM Tris-HCl, pH 7.4, 10 mM EDTA, 0.1% sodium dodecyl sulfate, 0.2% ficoll, 0.2% polyvinylpyrrolidone, 0.2% bovine serum albumin, and 50 µg/ml E. coil DNA as described in Ohno, S. et al., Proc. Natl. Acad. Sci. U.S.A. 78:5305–5309 (1980) except that the washing of the filter after hybridization was carried out in 3×SSC at 65° C.

From the positive clones clone pHIRF31 containing the longest cDNA insert was selected.

The desired cDNA sequence of clone pHIRF31 was isolated by digestion of the plasmid DNA by XhoI and after isolation subjected to sequencing by the methods described above. The structure of the human IRF-1 gene is shown in Formula II and in FIG. 8.

The sequences for the deduced murine and human IRF-1 are shown juxtaposed for comparison in FIG. 5.

Analysis of the human DNA revealed that this IRF-1 is shorter than the murine IRF-1 by four amino acids.

Strong conservation of the amino acid sequences can be seen between the two IRF-1 molecules. In particular, 133 out of 140 amino acids (95%) of the amino terminal halves can be seen to be identical.

Taken together, the above observation indicate that IRF-1 is a new class of DNA binding protein.

It should also be noted that the sequence ATTTATTTA and ATTTA, found in many cytokine and proto-oncogene mRNAs, are present within the 3' non-translated region of the murine IRF-1 CDNA, and likewise the sequence ATTTA is found within the corresponding region of the human IRF-1 cDNA. These sequences are believed to play a role in the post-transcriptional regulation of gene expression by confering instability to the mRNA (Shaw and Kamen, 1986; Caput et al., 1986).

Plasmid pIRF-L was transfected into *E.coli* MC1061/p3 which was deposited as *E.coli* MC106/p3 (pIRF-L) at the Fermentation Research Institute Agency of Industrial Science and Technology (FRI), 1-3, Higashi 1-chome, Tsukuba-shi, Ibaraki-ken 305, Japan, under the terms of the Budapest Treaty on 19th Aug. 1988 under No. FERM BP-2005.

Plasmid pIRF31 was similarly transfected into *E.coli* MC1061/p3 which was deposited as *E.coli* MC106/p3 (pIRP-31) at the FRI under the Budapest Treaty on 19th Aug. 1988 under No. FERM BP-2006.

Regulation of the IRF gene

1. Expression of IRF-1 mRNA

In view of the fact that IRF-1 manifests affinities to regulatory sequences of genes other than IFN-β gene and is thus involved in the regulation of a set of genes in various cell types, examination of the expression of the IRF-1 mRNA in mouse cells derived from various tissues and organs was carried out using the murine cDNA as a probe. To prepare this probe M13 mp10 phage DNA (see below) containing the sense strand of IRF-1 gene PstI fragment was used as a template to synthesise the $^{32}$p-labeled antisense DNA, the product was digested by EcoRI and the probe DNA isolated as described by Fujita et al. (1985).

Total RNA was isolated by the established procedure of Aruffo and Seed 1987.

The blotting analysis was then carried out essentially as described by Thomas (1980), the x-ray film being exposed for 3 days and the results are shown in FIG. 6A. The various lanes represent the results of runs carried out using whole cell RNA from the following tissue:

| Lane 1 | Brain |
| Lane 2 | Heart |
| Lane 3 | Liver |
| Lane 4 | Lung |
| Lane 5 | Spleen (unstimulated) |
| Lane 6 | Thymus |
| Lane 7 | Kidney |
| Lane 8 | Muscle |
| Lane 9 | Intestine |
| Lane 10 | Spleen (unstimulated) |
| Lane 11 | ConA - stimulated spleen |

In the run for each lane 5 μg of whole cell RNA was used, except in lane 8 for which only 1.2 μg RNA was used.

It will be seen from FIG. 6A that a band corresponding to about 2.0 kb was detected in most of the RNA samples by this blotting analysis, although the mRNA expression level seems low. It is noteworthy that the mRNA expression level in the spleen-derived lymphocytes was augmented dramatically following stimulation by ConA (Lane 11).

In a further assay mouse L929 cells were induced by NDV as described previously (Fujita et al., 1985) and the cytoplasmic RNA extracted, by the procedure of Aruffo and Seed 1987, every three hours after infection.

Probe DNAs were prepared from the following various sequences and labeled by the multiprime labeling reaction (Amersham), namely (i) an 1.8 kb EcoRI fragment from λL28-8 (specific activity $2 \times 10^8$ cpm/μg);

(ii) a 0.5 kb BamHI-BglII fragment from a mouse IFN-β genomic clone (specific activity $5 \times 10^8$ cpm/μg) and (iii) a 2.0 kb BamHI-PvuII fragment of a clone containing human β-actin pseudogene (specific activity $5 \times 10^8$ cpm/μg).

The results are shown in FIG. 6B. Blotting analysis was carried out, as described above, using the procedure of Thomas (1980).

Each lane received 10 μg of the cytoplasmic RNA. The x-ray film was exposed for 3 hours. Densitometric analysis revealed that IRF-1 mRNA increased about 25-fold, 9–12 hours after NDV infection.

Whilst the increase in mRNA is dramatic it is transient, peaking at 9 to 12 hours and levelling off 15 hours after induction. mRNA accumulation preceeds the accumulation of the IFN-β mRNA; as can be seen from FIG. 6B the induction of the IRF-1 mRNA can be observed already 3 hours after NDV infection, while the IFN-β mRNA is detectable only after 6 hours under similar blotting conditions for both RNAs.

The IRF-1 promoter

As demonstrated above, the IRF-1 gene is transcriptionally regulated by various agents such as viruses and mitogenes.

Southern blot analysis of the chromosomal DNA indicated that the IRF-1 gene may be spliced and not multi-membered in the mouse.

A λ-phage library containing new-born mouse DNA was screened for the clones harboring the IRF-1 promoter sequence using the same λL28-8 derived cDNA probe used above. Four positive clones were identified, all of which were found to contain the same genomic DNA and one of them λg14-2 was used for further analysis. A PstI fragment was sub-cloned into the PstI site of pUC19 to construct p19IRFP.

The same DNA was thereafter cloned into the PstI site of M13mp10 and M13mp11 which were used to generate DNA for sequence analysis.

Nucleotide sequence analysis of the PstI fragment from the above clones was carried out as previously described. Major and minor CAP sites were identified by S1 mapping analysis.

The determined sequence is shown in FIG. 7A. As can be seen the downstream sequence of the DNA perfectly matches that of the pIRF-L derived cDNA.

The S1 nuclease analysis indicates the presence of two CAP sites for the IRF-1 mRNA in which the major site is about 20 nucleotides downstream of the minor site. Typical TATA box sequences are not present within the upstream region of the gene. In view of the unusual abundancy of CpG sequence, this region probably constitutes an "HTF island" (Bird, 1986).

The promoter region contains two GC boxes and one CAAT box (see FIG. 7A); the former boxes should bind SpI (Kadogan et al., 1986) and the latter, CP-1 or CP-2 (Chodosh et al., 1988).

The PstI fragment containing the promoter sequences was then tested for its reactivity in response to extracellular signals e.g. virus inducibility in the following manner:

A chimeric gene was constructed in which a reporter gene, namely a bacterial chloramphenicol acetyltransferase (CAT) gene was abutted downstream of the PstI segment. This was done by excising a PstI fragment from P19IRFP (see above) by BamHI and HindIII and cloning the resulting fragment into the BglII-HindIII backbone fragment of pA$_{10}$cat$_2$ (Rosenthal et al., 1983) to construct pIRFcat.

Several further constructs were prepared as follows:

pIRFΔcat was prepared by digesting the p19IRFP-derived BamHI-HindIII fragment with HaeIII whose single recognition site is located at −30 to −35 from the major CAP site (FIG. 7A). The resulting HaeIII-HindIII fragment was ligated with the BglII-HindIII backbone fragment of pA$_{10}$cat$_2$ and the following synthetic DNA

```
5'GATCCTGATTTCTTCGCGGCGC 3'
    3'GATCTAAAGAAGCGC 5'
```

Thus both pIRFcat and pIRFΔcat contained sequences up to −320 and −48 from the major CAP site respectively.

p-125cat contains the promoter sequence of the human IFN-β gene as described by Fujita et al., 1987.

pSV2cat is described in Gorman et al., Science, Vol. 221, pp 551–553.

As a reference gene PRSVgpt was used (see Gorman et al., above).

The various genes were transfected into mouse L929 cells using the calcium phosphate method (Fujita et al., 1985). 5×10$^6$ cells were transfected with 7.5 μg of the test plasmid containing the CAT reporter gene and 2.5 μg of pRSVgpt. The cells were induced by NDV or mock-induced and then subjected to the enzyme assay as described by Fujita et al., 1985.

In calculating the relative CAT activity, CAT activity from the mock-induced cells, transfected with pSV2cat was taken as 100%. Each CAT activity was normalised by the Eco gpt (Mulligan and Berg, Proc. Natl. Acad. Sci. U.S.A., Vol. 78, pp 2072–2076) of the respective samples. In samples where the CAT was below the background level, they were marked as b.b.

Figure 7B:
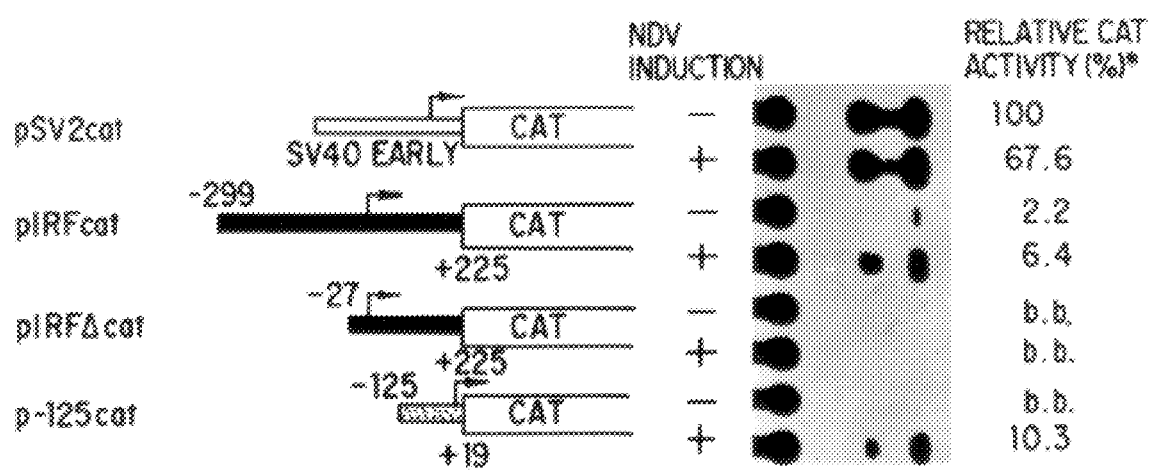

The results are shown in FIG. 7B.

It will be seen that transfection of the pIRFcat into mouse L929 gave rise to the expression of low level CAT activity. The CAT expression level was increased when the transfected cells were stimulated by NDV. Deletion of the 300 bp upstream sequence of the IRF-1 gene (pIRFΔcat) virtually abolished both constitutive and induced expression of the CAT gene. This demonstrates that the promoter sequence lies within the 300 bp upstream region and is virus inducible.

Construction of expression plasmids

1. Phage DNA of clone λL28-8 was digested by EcoRI and the cDNA insert was recovered. The EcoRI sites of the cDNA were rendered flush by T4 DNA polymerase and then ligated with synthetic adaptor DNAs having the sequence pGATCCATTGTGCTGG and pCCAGCACAATG according to Aruffo and Seed, 1987.

After removal of the synthetic DNAs by 5–20% potassium acetate gradient centrifugation (Aruffo and Seed, 1987), the IRF-1 cDNA with the adaptor DNAs attached to both its ends was ligated with BstXI-cleaved CDM8 vector DNA (Seed, B., Nature, vol. 329, pp 840–842, 1987). Plasmids pIRF-S and pIRF-A containing the IRF-1 cDNA in the sense and antisense orientation with respect to the CMV promoter respectively were isolated.

Each plasmid DNA was co-transfected with either p-55cat or p55C1B (Fujita et al., 1987) into L929 cells and the CAT expression level was determined.

The results are shown in Table 1 below:

TABLE 1

| | Transfected plasmids | Induction by NDV | CAT activity (% conversion) |
|---|---|---|---|
| Exp. 1 | pIRF-S<br>p-55cat | − | <1% |
| | pIRF-S<br>p-55C1B | − | 50 % |
| | pIRF-A<br>p-55cat | − | <1% |
| | pIRF-A<br>p-55C1B | − | <1% |
| | pIRF-S<br>p-55C1B | − | 1,7% |
| | pIRF-S<br>p-55C1B | + | 3,6% |
| Exp. 2 | pIRF-A<br>p-55C1B | − | <0,1% |
| | pIRF-A<br>p-55C1B | + | <0,1 % |

The DNA transfection efficiency varies depending on the state of the recipient cells (in this case, mouse L929 cells). The efficiency was much lower in Exp. 2 compared to Exp. 1. Therefore, the CAT expression level is relatively lower in Exp. 2.

As can be seen from the above table significant CAT activity was detectable only in the cells transfected by p-55CIB and pIRF-S. They demonstrate that the IRF-1 binds to the repeated (8 times) AAGTGA sequences present in the upstream of the CAT gene in p-55CIB and thereby promotes transcription of the distal CAT gene.

The results further show that the CAT expression level is increased (more than two fold) by infecting the transfected cells with NDV (Table 1), demonstrating that it is possible to control the gene expression by various stimuli such as viruses.

An expression plasmid for the production of a protein consisting of IRF-1 DNA binding domain and transcriptional activation domain of yeast GAL4 was constructed as follows:

Plasmid PIRF-S was digested by HindIII and PstI and the cDNA insert isolated. The cDNA was digested by DraIII and the HindIII-DraIII fragment (about 550 bp) was recovered and designated Fragment A.

The expression vector CDM8 was digested by HindIII and XbaI and the backbone DNA isolated and designated Fragment B.

The DNA encoding the yeast GAL4 transcriptional activation domain was isolated from plasmid pRB968 (Ma and Ptashne, 1987) as follows:

The pRB968 DNA was first digested by HindIII and the termini were rendered flush by T4 DNA polymerase. Synthetic XbaI linker DNA was added to the DNA and the DNA was subsequently digested by PvuII and XbaI.

The resulting ca. 600 bp PvuII-XbaI DNA fragment was recovered and designated Fragment C.

In addition, a synthetic DNA with the following sequence was prepared:

(5') GTGTCGTCCAG (3')
(3') GCACACAGCAGGTC (5')

designated Fragment D.

An expression vector pIRFGAL4 was constructed by ligating the Fragments A, B, C and D. As a control plasmid, plasmid PIRFΔGAL4 was constructed by ligating Fragments A, B, C and a synthetic DNA with the following sequence:

(5') GTGTCTGACAG (3')
(3') GCACACAGACTGTC (5')

As a terminator triplet, TGA, is present in frame between the IRF-1 and GAL4 sequences in pIRFΔGAL4, the expressed protein should lack the GAL4 activation domain.

In order to test the functional properties of the plasmid encoded chimeric transcriptional factor pIRFGAL4 and pIRFΔGAL4 were each co-transfected with p-55CIB into L929 cells and CAT expression monitored. The results are shown in Table 2 below:

TABLE 2

| Transfected plasmid | CAT activity (% conversion) |
|---|---|
| pIRF-s p-55C1B | 2,0% |
| pIRF-A p-55C1B | <0,2% |
| pIRFGAL p-55C1B | 1,4% |
| pIRF Δ GAL4 p-55C1B | <0,2% |

Host cell, Mouse L929 cells. Cells were not induced by NDV.

The results show that the expression of a target gene (such as a genes encoding an interleukin, an interferon ($\alpha$, $\beta$ and $\gamma$), a plasminogen activator, erythropoietin, granulocyte colony stimulating factor, insulin, human growth hormone or superoxide dismutase (or mutants of the human genes) can be augmented by IRF-1.

Target genes as mentioned above, such as interferon genes e.g. IFN-$\alpha$, IFN-$\beta$, IFN-$\gamma$, IFN-omega and plasminogen activators e.g. t-PA, pro-urokinase or urokinase etc. can be expressed more efficiently also by including therefor promoters fused with various lengths of recognition sequences for IRF-1, e.g. AAGTGA.

For example the target genes can be introduced into various host cells, together with either intact IRF-1 or chimeric IRF-1 genes. By increasing the length of IRF-1 recognition site DNA e.g. by increasing the number of AAGTGA repeats and the expression level of the transcription factor a high-level expression of the target genes can be achieved.

For example the AAGTGA repeat sequences can be abutted to a suitable promoter such as IFN-$\beta$ promoter or SV40 virus early promoter. A target gene e.g. a t-PA gene or IFN-$\beta$ gene can be linked downstream of such a promoter; the structure of such a constructed gene would be (AAGTGA)$_x$ (Promoter) (target gene e.g. t-PA gene).

Such a gene could then be introduced into and amplified in CHO cells e.g. CHO DXBII (dhfr-strain) cells (Urlaub and Chasin, Proc. Natl., Acad. Sci., U.S.A., Vol. 77, pp 4216–4220, 1980).

Ideally, as discussed above, a host cell will be chosen from a cell which has no or substantially no level of endogenous IRF-1 activity. The IRF-1 gene, preferably either with a strong promoter such as CMV promoter or an inducible promoter such as metallothionen gene promoter can be introduced into the various host cells in a conventional manner.

The IRF-1 gene can be co-introduced and amplified together with the target gene. Alternatively the IRF-1 gene and the target gene can be separately introduced into the host cell.

In such transfected cells, IRF-1 may be produced either constitutively (in the case of e.g. CMV promoter) or in an induced manner (in the case of e.g. the metallothionen promoter it is induced by divalent metals such as zinc). The expressed IRF-1 binds to the AAGTGA repeats and augments the distal target gene e.g. t-PA gene or IFN gene.

Such expression could be further augmented by virus e.g. NDV induction, as can be seen from Table 1, Experiment 2 such induction increases the activity of the IRF-1.

Mouse cDNA sequence which cross-hybridises with murine IRF-1 cDNA of Formula III A mouse cDNA library was prepared by the procedure described above. The cDNA was synthesised by the standard procedure using the mouse L929 cell-derived mRNA and the CDNA was inserted into the $\lambda$gt11 vector by the standard procedure. The resulting $\lambda$gt11 library was then screened to isolate cDNA clones whose inserts cross-hybridize with the murine IRF-1 cDNA described above, as follows:

Nitrocellulose filters containing the phage plaque DNAs were incubated in the following stages
(1) in 3×SCC at 65° C. for 30 minutes, followed by
(2) 60 minutes incubation in 3×SSC containing Denhart's solution (0.2% bovine serum albumin, 0.2% Ficoll, 0.2% polyvinylpyrrolidone 25), followed by
(3) a pre-hybridisation step consisting of incubation for 12 hours at 65° C. in a solution containing 1M NaCl, 50 mM Tris-HCl, pH 8.0, 10 mM EDTA, 0.1% SDS, 50 $\mu$g/ml single stranded carrier DNA (e.g. salmon sperm DNA) and Denhart's solution and
(4) the stage 3 incubation was repeated but including $^{32}$p-labeled murine IRF-1 cDNA as a probe. This cDNA probe was prepared as the EcoRI cleaved insert from $\lambda$L-28-8 and translated by the Multiprime labeling system (see above). The incubation was carried out at 65° C. for 12 hours.

The filters were then washed, rinsed briefly in 2×SCC solution and then washed in 3×SCC solution containing 0.1% SDS for 30 minutes at 65° C. This procedure was twice repeated.

One of the positive clones, designated pHH-45 was selected and was revealed to contain cDNA covering only part of a coding sequence for an IRF.

The cDNA insert in PHH-45 was therefore isolated and used to screen clones containing larger inserts as described above for the preparation of pIRF-L under the heading "Structure of the cDNA encoding murine IRF-1".

Of the positive clones identified the one designated pIRF2-5 was selected and characterised using the procedure previously described for murine IRF-1. The complete hybridizing cDNA sequence is shown in formula IVa and the amino acid sequence of the corresponding IRF protein is shown in formula VIII.

Plasmid pIRF 2-5 was transfected into *E.coli* MC 1061/p3 which was deposited as *E.coli* at the FRI under the Budapest Treaty on 22 Nov. 1988 under No. FERM BP-2157.

cDNA from the yeast genome which hybridizes with human IRF-1 cDNA sequence

Yeast DNA was prepared by the standard procedure and digested with EcoRI. 5 μg of the digested DNA was loaded onto 0.8% agarose gel and subjected to electrophoresis and DNA blotting by standard procedures.

Figure 9A:
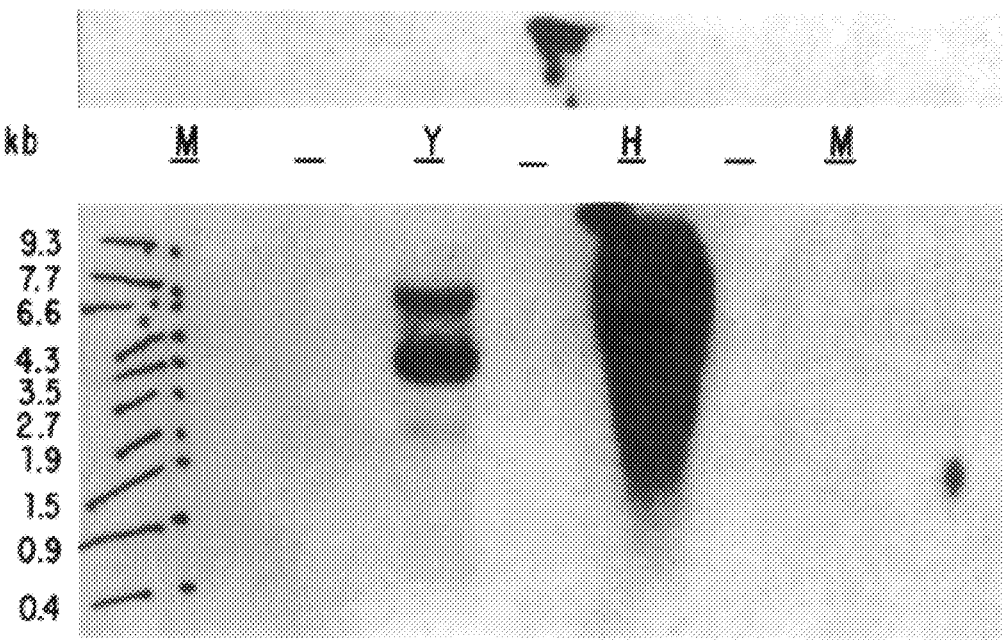
FIG. 9: Identification of DNA sequences present in yeast that cross-hybridize with human IRF-1 cDNA.
Figure 9B:
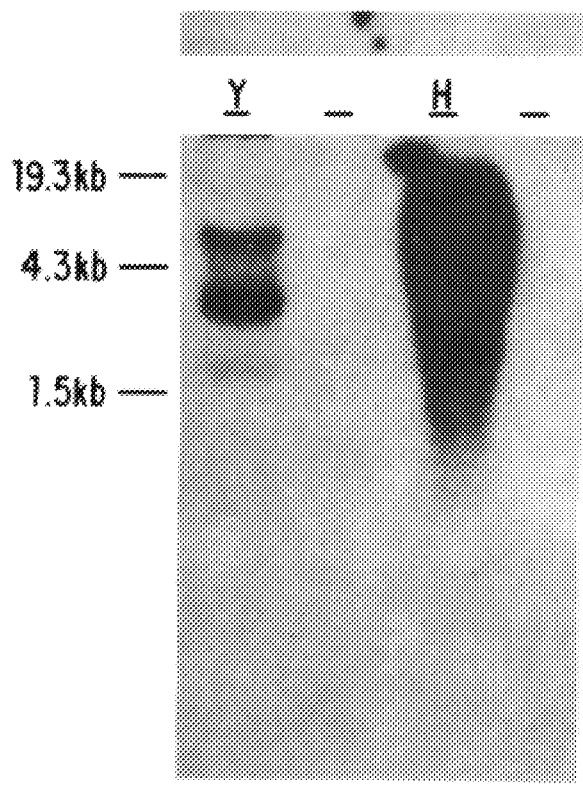

The blotted filter was treated exactly as described in the preceding example for isolating mouse DNA which hybridizes with murine IRF-1, except as follows:

In step (3) the incubation temperature was 55° C. and in step (4) the incubation was also carried out at 55° C. and the radioactive probe was the human IRF-1 cDNA isolated from pHIRF31 by XhoI digestion of the plasmid, this probe being labeled as described in the preceding example for murine IRF-1. The filter was washed at 55° C. in 2×SSC. The positive clones were identified by autoradiography (see FIG. 9).

REFERENCES

Abreu S. L., Bancroft F. C., and Stewart II E. W. (1979). Interferon priming. J. Biol. Chem. 254, 414–418.

Aruffo A., and Seed B. (1987). Molecular cloning of a cDNA by a high-efficiency COS cell expression system. Proc. Natl. Acad. Sci. U.S.A. 84, 8573–8577.

Bird A. P. (1986). CpG-rich islands and the function of DNA methylation. Nature 321, 209–213.

Caput D., Beutler B., Hartog K., Thayer R., Brown-Schimer S., and Cerami A. (1986). Identification of a common nucleotide sequence in the 3' untranslated region of mRNA molecules specifying inflammatory mediators. Proc. Natl. Acad. Sci U.S.A. 83, 1670–1674.

Cavalieri R. L., Havell E. Z., Vilcek J., and Pestka S. (1977). Induction and decay of human fibroblast interferon mRNA. Proc. Natl. Acad. Sci. U.S.A. 74, 4415–4419.

Chodosh L. A., Baldwin A. S., Carthew R. W., and Sharp P. A. (1988). Human CCAAT-binding proteins have heterologous subunits. Cell 53, 11–24.

Dinter H., Hauser H., Mayr U., Lammers R., Bruns W., Gross G., and Collins J. (1983). Human interferon-beta and co-induced genes: molecular studies. In the biology of the Interferon System 1983, E. De Maeyer and H. Schellekens, eds. (Amsterdam: Elsevier Science Publishers), 33–34.

Dinter H., and Hauser H. (1987). Cooperative interaction of multiple DNA elements in the human interferon-β promoter. Eur. J. Biochem. 166, 103–109.

Evans R. M., and Hollenberg S. M. (1988). Zinc Fingers: Gilt by association. Cell 52, 1–3.

Fujita T., Saito S., and Kohno S. (1979). Priming increases the amount of interferon mRNA in poly(rI):poly (rC)-treated L cells. J. Gen. Viol. 45,301–308.

Fujita T., Ohno S., Yasumitsu H., and Taniguchi T. (1985). Delimination and properties of DNA sequences required for the regulated expression of human interferon-β gene Cell 41, 489–496.

Fujita T., Shibuya H., Hotta H., Yamanishi K., and Taniguchi T. (1987). Interfero-β gene regulation: Tandemly repeated sequences of a synthetic 6 bp oligomer function as a virus-inducible enhancer. Cell 49, 357–367.

Galabru J., and Hovanessian A. G. (1985). Two interferon-β indeced proteins are involved in the protein kinase complex dependent on double-stranded RNA. Cell 43, 685–694.

Goodbourn S., Zinn K., and Maniatis T. (1985). Human β-interferon gene expression is regulated by an inducible enhancer element. Cell 41, 509–520.

Huynh T. V., Young R. A., and Davis R. W. (1985). Constructing and screening cDNA libraries in gt10 and 11. In DNA cloning-A Practical Approach, Volume 1, D. M. Glover, ed. (Oxford: IRL Press), pp. 49–78.

Israel A., Kimura A., Fournier A., Fellous M., and Kourilsky P. (1986). Interferon response sequence potentiates activity of an enhancer in the promoter region of a mouse H-2 gene. Nature 322, 743–746.

Kadonaga J. T., Jones K. A., and Tjian R. (1986). Promoter-specific activation of RNA polymerase II transcription by Sp 1. Trends Biochem. Sci. 11, 20–23.

Kakidani H., and Ptashne M. (1986). GAL4 activates gene expression in mammalian cells. Cell 52, 161–167.

Keller A. D., and Maniatis T. (1988). Identification of an inducible factor that binds to a positive regulatory element of the human β-interferon gene. Proc. Natl. Acad. Sci U.S.A. 85, 3309–3313.

Kohase M., May L. T., Tamm I., Vilcek J., and Sehgal P. B. (1987). A cytokine network in human diploid fibroblasts: interactions of beta interferons, tumor necrosis factor, platelet-derived growth factor and interleukin-1. Mol. Cell. Biol. 7, 272–280.

Korber B., Mermod N., Hood L., and Stroynowski I. (1988). Regulation of gene expression by interferons: Control of H-2 Promoter responses. Science 239, 1302–1306.

Kozak M. (1987). An analysis of 5'-noncoding sequences from 699 vertebrate messenger RNAs. Nucl. Acids Res. 15, 8125–8143.

Krebs E., Eisenman R., Kuenzel E., Litchfield D., Lozeman F., Liischer B., and Sommercorn J. (1988). Casein Kinase II as a potentially important enzyme concerned with signal transduction. In the Molecular Biology of Signal Transduction (Cold Spring Harbor, N.Y.: Cold Spring Harbor Laboratory) Abstract p.35.

Kuhl D., de la Fuente J., Chaturvedi M., Parimoo S., Ryals J., Mayer F., and Weissmann C. (1987). Reversible silencing of enhancers by sequences derived from the human IFN-α promoter. Cell 50, 1057–1069.

Kyte J., and Doolittle R. F. (1982). A simple method for displaying the hydropathic character of a protein. J. Mol. Biol. 157, 105–132.

Levy D. E., Kessler D. S., Pine R., Reich N., and Darnell J. E. (1988). Interferon-induced nuclear factors that bind a shared promoter element correlate with positive and negative transcriptional control. Genes and Development 2, 383–393.

Ma J., and Ptashne M. (1987). The carboxy-terminal 30 amino acids of GAL4 are recognised by GAL80. Cell 50, 137–142.

Maxam A., and Gilbert W. (1980). Sequencing end-labeled DNA with base specific chemical cleavages. Meth. Enzym. 65, 499–560.

Moore R. N., Larsen H. S., Horohov D. W., and Rouse B. T. (1984). Endogenous regulation of macrophase proliferative expansion by colony-stimulation-factor-induced interferon. Science 223, 178–180.

Nedwin G., Naylor S., Sakaguchi A., Smith D., Jarrett-Nedsin J., Pennica D., Goeddel D., and Gray P. (1985). Human lymphotoxin and tumor necrosis factor genes: structure, homology and chromosomal localisation. Nucl. Acids Res. 13, 6361–6373.

Nir U., Cohen B., Chen L., and Revel M. (1984). A human IFN-β1 gene deleted of promoter sequences upstream from the TATA box is controlled post-transcriptionally by dsRNA. Nucl. Acids Res. 12, 6979–6993.

Ohno S., and Taniguchi T. (1983). The 5'-flanking sequence of human interferon-β gene is responsible for viral induction of transcription. Nucl. Acids Res. 11, 5403–5412.

Onozaki K., Urawa H., Tamatani T., Iwamura Y., Hashimoto T., Baba T., Suzuki H., Yamada M., Yamamoto S., Oppenheim J. J., and Matsushima K. (1988).Synergistic interactions of interleukin 1, interferon-β and tumor necrosis factor in terminally differentiating a mouse myeloid leukemic cell line (M1). J. Immunol. 140, 112–119.

Pabo C. O., and Sauer R. T. (1984). Protein-DNA recognition. Ann. Rev. Biochem. 53, 293–321.

Raji N. B. K., and Pitha P. M. (1981). An analysis of interferon mRNA in human fibroblast cells induced to produce interferon. Proc. Natl. Acad. Sci U.S.A. 78, 7426–7430.

Raji N. B. K., and Pitha P. M. (1983). Two levels of regulation of β-interferon gene expression in human cells. Proc. Natl. Acad. Sci U.S.A. 80, 3923–3927.

Resnitzky D., Yarden A., Zipori D., and Kimchi A. (1986). Autocrine β-related interferon controls c-myc suppression and growth arrest during hematopoietic cell differentiation. Cell 46, 31–40.

Rosenthal N., Kress M., Gruss P., and Khoury G. (1983). BK viral enhancer element and a human cellular homolog. Science 222, 749–755.

Ryals J., Dieks P., Ragg H., and Weissmann C. (1985). A 46-nucleotide promoter segment from an INF-α gene renders an unrelated promoter inducible by virus. Cell 41, 497–507.

Shaw G., and Kamen R. (1986). A conserved AU sequence from the 3' untranslated region of GM-CSF mRNA mediates selective mRNA degradation. Cell 46, 659–667.

Singh H., LeBowitz J. H., Baldwin Jr. A. S., and Sharp P. A. (1988). Molecular cloning of an enhancer binding protein: Isolation by screening of an expression library with a recognition site DNA. Cell 52 415–423.

Sugita K., Miyazaki J. I., Appella E., and Ozato K. (1987). Interferons increase transcription of a major histocompatibility class I gene via a 5' interferon consensus sequence. Mol. Cell. Biol. 7, 2625–2630.

Taniguchi T., Matsui H., Fujita T., Takaoka C., Kashima N., Yoshimoto R., and Hamuro J. (1983). Structure and expression of a cloned cDNA for human interleukin-2. Nature 302, 305–310.

Taniguchi T. (1988). regulation of cytokine gene expression. Ann. Rev. Immunol. 6, 439–464.

Thomas P. S. (1980). Hybridisation of denatured RNA and small DNA fragments transferred to nitrocellulose. Proc. Natl. Acad. Sci. U.S.A. 77, 5201–5205.

Tiwari R. J., Kusari J., and Sen G. C. (1987). Functional equivalents of interferon-mediated signals needed for induction of a mRNA can be generated by double-stranded RNA and growth factors. EMBO J. 6, 3373–3378.

Warren M. K., and Ralf P. (1986). Macrophage growth factor CSF-1 stimulates human monocyte production of interferon, tumor necrosis factor and colony stimulating activity. J. Immunol. 137, 2281–2285.

Webster N., Jin J. R., Green S., Hollis M., and Chambon P. (1988). The yeast UAGs is a transcriptional enhancer in human HeLa cells in the presence of the GAL4 trans-activator. Cell 52, 169–178.

Weissmann C., and Weber H. (1986). The interferon genes. Proc. Natl. Acid Res. Mol. Biol., 33, 251–300.

Young R. A., and Davis R. W. (1983). Yeast RNA polymerase II genes: Isolation with antibody probes. Science 222, 778–782.

Zinn K., Dimaio D., and Maniatis T. (1983). Identification of two distinct regulatory regions adjacent to the human β-interferon gene. Cell 34, 865–879.

Zullo J. N., Cochan B. H., Huang A. S., and Stiles C. D. (1985). Platelet-derived growth factor and double-stranded ribonucleic acids and stimulate expression of the same genes in 3T3 cells. Cell 43, 793–800.

We claim:

1. A composition comprising proteins extracted from a recombinant host cell, wherein said composition comprises a recombinant IRF-1 protein produced by said cell and wherein said IRF-1 can bind to (a) a first recognition sequence (AAGTGA)$_4$ and (b) a second recognition sequence that is at bases −64 to −100 of the human IFN-β gene, wherein said binding in step (a) and (b) augments transcription of a coding sequence operably linked to a promoter that contains said first or second recognition sequence, and wherein said IRF-1 protein is encoded by a recombinant nucleic acid sequence in said host cell that hybridizes to the anti sense sequence of a DNA selected from the group consisting of

```
           10        20
ATGCCCATCACTTGGATGCGCATGAGA 30        40        50
          CCCTGGCTAGAGATGCAGATTAA 60        70
TTCCAACCAAATCCCGGGGCTCATCTG 80        90       100
          GATTAATAAAGAGGAGATGATCT 110       120
TGGAGATCCCATGGAAGCATGCTGCCA 130       140       150
          AGCATGGCTGGGACATCAACAAG 160       170
GATGCCTGTTTGTTCCGGAGCTGGGCC 180       190       200
          ATTCACACAGGCCGATACAAAGC 210       220
AGGGGAAAAGGAGCCAGATCCCAAGAC 230       240       250
          GTGGAAGGCCAACTTTCGCTGTG 260       270
CCATGAACTCCCTGCCAGATATCGAGG 280       290       300
          AGGTGAAAGACCAGAGCAGGAAC 310       320
AAGGGCAGCTCAGCTGTGCGAGTGTAC 340       340       350
          CGGATGCTTCCACCTCTCACCAA 360       370
GAACCAGAGAAAAGAAAGAAAGTCGAA 380       390       400
          GTCCAGCCGAGATGCTAAGAGCA 410       420
AGGCCAAGAGGAAGTCATGTGGGGATT 430       440       450
          CCAGCCCTGATACCTTCTCTGAT 460       470
GGACTCAGCAGCTCCACTCTGCCTGAT
```

-continued

```
            480       490       500
                 GACCACAGCAGCTACACAGTTCC
       510       520
AGGCTACATGCAGGACTTGGAGGTGGA
                 530       540       550
                 GCAGGCCCTGACTCCAGCACTGT
       560       570
CGCCATGTGCTGTCAGCAGCACTCTCC
                 580       590       600
                 CCGACTGGCACATCCCAGTGGAA
       610       620
GTTGTGCCGGACAGCACCAGTGATCTG
                 630       640       650
                 TACAACTTCCAGGTGTCACCCAT
       660       670
GCCCTCCATCTCTGAAGCTACAACAGA
                 680       690       700
                 TGAGGATGAGGAAGGGAAATTAC
       710       720
CTGAGGACATCATGAAGCTCTTGGAGC
                 730       740       750
                 AGTCGGAGTGGCAGCCAACAAAC
       760       770
GTGGATGGGAAGGGGTACCTACTCAAT
                 780       790       800
                 GAACCTGGAGTCCAGCCCACCTC
       810       820
TGTCTATGGAGACTTTAGCTGTAAGGA
                 830       840       850
                 GGAGCCAGAAATTGACAGCCCAG
       860       870
GGGGGGATATTGGGCTGAGTCTACAGC
                 880       890       900
                 GTGTCTTCACAGATCTGAAGAAC
       910       920
ATGGATGCCACCTGGCTGGACAGCCTG
                 930       940       950
                 CTGACCCCAGTCCGGTTGCCCTC
       960       970
CATCCAGGCCATTCCCTGTGCACCG
      and

ATG CCA ATC ACT CGA ATG CGG ATG

AGA CCC TGG CTA GAG ATG CAG ATT

AAT TCC AAC CAA ATC CCA GGG CTG

ATC TGG ATC AAT AAA GAA GAG ATG

ATC TTC CAG ATT CCA TGG AAG CAC

GCT GCT AAG CAC GGC TGG GAC ATC

AAC AAG GAT GCC TGT CTG TTC CGG
```

-continued

```
             AGC TGG GCC ATT CAC ACA GGC CGA

TAC AAA GCA GGA GAA AAA GAG CCA

GAT CCC AAG ACA TGG AAG GCA AAC

TTC CGT TGT GCC ATG AAC TCC CTG

CCA GAC ATC GAG GAA GTG AAG GAT

CAG AGT AGG AAC AAG GGC AGC TCT

GCT GTG CGG GTG TAC CGG ATG CTG

CCA CCC CTC ACC AGG AAC CAG AGG

AAA GAG AGA AAG TCC AAG TCC AGC

CGA GAC ACT AAG AGC AAA ACC AAG

AGG AAG CTG TGT GGA GAT GTT AGC

CCG GAC ACT TTC TCT GAT GGA CTC

AGC AGC TCT ACC CTA CCT GAT GAC

CAC AGC AGT TAC ACC ACT CAG GGC

TAC CTG GGT CAG GAC TTG GAT ATG

GAA AGG GAC ATA ACT CCA GCA CTG

TCA CCG TGT GTC GTC AGC AGC AGT

CTC TCT GAG TGG CAT ATG CAG ATG

GAC ATT ATA CCA GAT AGC ACC ACT

GAT CTG TAT AAC CTA CAG GTG TCA

CCC ATG CCT TCC ACC TCC GAA GCC

GCA ACA GAC GAG GAT GAG GAA GGG

AAG ATA GCC GAA GAC CTT ATG AAG

CTC TTT GAA CAG TCT GAG TGG CAG

CCG ACA CAC ATC GAT GGC AAG GGA

TAC TTG CTC AAT GAG CCA GGG ACC

CAG CTC TCT TCT GTC TAT GGA GAC

TTC AGC TGC AAA GAG GAA CCA GAG
```

```
                    ATT GAC AGC CCT CGA GGG GAC ATT

GGG ATA GGC ATA CAA CAT GTC TTC

ACG GAG ATG AAG AAT ATG GAC TCC

ATC ATG TGG ATG GAC AGC CTG CTG

GGC AAC TCT GTG AGG CTG CCG CCC

TCT ATT CAG GCC ATT CCT TGT GCA CCA TAG
``` when the hybridization is performed at 65 degrees Centigrade for 20 hours in a medium consisting essentially of 1M NaCl, 50 ml Tris-HCl, pH 7.4, 10 mM EDTA, 0.1% sodium dodecyl sulfate, 0.2% ficoll, 0.2% polyvinylpyrrolidone, 0.2% bovine serum albumin, 50 μg/ml *E. coli* DNA, said nucleic acid sequence and said antisense sequence.

2. The composition of claim 1, wherein the amino acid sequence of said IRF-1 is

MetProIleThrTrpMetArgMetArgProTrpLeuGluMet
GlnIleAsnSerAsnGlnIleProGlyLeuIleTrpIleAsnLysGluGluMetIleLeu
GluIleProTrpLysHisAlaAlaLysHisGlyTrpAspIleAsnLysAspAlaCysLeu
PheArgSerTrpAlaIleHisThrGlyArgTyrLysAlaGlyGluLysGluProAspPro
LysThrTrpLysAlaAsnPheArgCysAlaMetAsnSerLeuProAspIleGluGluVal
LysAspGlnSerArgAsnLysGlySerSerAlaValArgValTryArgMetLeuProPro
LeuThrLysAsnGlnArgLysGluArgLysSerLysSerSerArgAspAlaLysSerLys
AlaLysArgLysSerCysGlyAspSerSerProAspThrPheSerAspGlyLeuSerSer
SerThrLeuProAspAspHisSerSerTyrThrValProGlyTyrMetGlnAspLeuGlu
ValGluGlnAlaLeuThrProAlaLeuSerProCysAlaValSerSerThrLeuProAsp
TrpHisIleProValGluValValProAspSerThrSerAspLeuTyrAsnPheGlnVal
SerProMetProSerIleSerGluAlaThrThrAspGluAspGluGluGlyLysLeuPro
GluAspIleMetLysLeuLeuGluGlnSerGluTrpGlnProThrAsnValAspGlyLys
GlyTryLeuLeuAsnGluProGlyValGlnProThrSerValTyrGlyAspPheSerCys
LysGluGluProGluIleAspSerProGlyGlyAspIleGlyLeuSerLeuGlnArgVal
PheThrAspLeuLysAsnMetAspAlaThrTrpLeuAspSerLeuLeuThrProValArg
LeuProSerIleGlnAlaIleProCysAlaPro.

3. The composition of claim 2, wherein said nucleic acid sequence comprises

```
              10         20         30         40         50
    ATGCCCATCACTTGGATGCGCATGAGACCCTGGCTAGAGATGCAGATTAA
              60         70         80         90        100
    TTCCAACCAAATCCCGGGGCTCATCTGGATTAATAAAGAGGAGATGATCT
             110        120        130        140        150
    TGGAGATCCCATGGAAGCATGCTGCCAAGCATGGCTGGGACATCAACAAG
             160        170        180        190        200
    GATGCCTGTTTGTTCCGGAGCTGGGCCATTCACACAGGCCGATACAAAGC
             210        220        230        240        250
    AGGGGAAAAGGAGCCAGATCCCAAGACGTGGAAGGCCAACTTTCGCTGTG
             260        270        280        290        300
    CCATGAACTCCCTGCCAGATATCGAGGAGGTGAAAGACCAGAGCAGGAAC
             310        320        340        340        350
    AAGGGCAGCTCAGCTGTGCGAGTGTACCGGATGCTTCCACCTCTCACCAA
             360        370        380        390        400
    GAACCAGAGAAAAGAAAGAAAGTCGAAGTCCAGCCGAGATGCTAAGAGCA
             410        420        430        440        450
    AGGCCAAGAGGAAGTCATGTGGGGATTCCAGCCCTGATACCTTCTCTGAT
             460        470        480        490        500
    GGACTCAGCAGCTCCACTCTGCCTGATGACCACAGCAGCTACACAGTTCC
             510        520        530        540        550
    AGGCTACATGCAGGACTTGGAGGTGGAGCAGGCCCTGACTCCAGCACTGT
             560        570        580        590        600
    CGCCATGTGCTGTCAGCAGCACTCTCCCCGACTGGCACATCCCAGTGGAA
             610        620        630        640        650
    GTTGTGCCGGACAGCACCAGTGATCTGTACAACTTCCAGGTGTCACCCAT
             660        670        680        690        700
    GCCCTCCATCTCTGAAGCTACAACAGATGAGGATGAGGAAGGGAAATTAC
             710        720        730        740        750
    CTGAGGACATCATGAAGCTCTTGGAGCAGTCGGAGTGGCAGCCAACAAAC
```

```
            760       770       780       790       800
GTGGATGGGAAGGGGTACCTACTCAATGAACCTGGAGTCCAGCCCACCTC 810       820       830       840       850
TGTCTATGGAGACTTTAGCTGTAAGGAGGAGCCAGAAATTGACAGCCCAG 860       870       880       890       900
GGGGGGATATTGGGCTGAGTCTACAGCGTGTCTTCACAGATCTGAAGAAC 910       920       930       940       950
ATGGATGCCACCTGGCTGGACAGCCTGCTGACCCCAGTCCGGTTGCCCTC 960       970
CATCCAGGCCATTCCCTGTGCACCG.
```

4. The composition of claim 3, wherein said nucleic acid sequence comprises upstream and downstream sequences that flank the sequence encoding said IRF-1, and said upstream and downstream sequences and said IRF-1 encoding sequences comprise

```
        CGAGCCCCGCCGAACCGAGGCCACCCGGAGCCGTGCCCAGTCCACGC

CGGCCGTGCCCGGCGGCCTTAAGAACCAGGCAACCACTGCCTTCTTCCCT

CTTCCACTCGGAGTCGCGCTTCGCGCGCCCTCACTGCAGCCCCTGCGTCG

CCGGGACCCTCGCGCGCGACCAGCCGAATCGCTCCTGCAGCAGAGCCAAC 10        20        30        40        50
ATGCCCATCACTTGGATGCGCATGAGACCCTGGCTAGAGATGCAGATTAA 60        70        80        90       100
TTCCAACCAAATCCCGGGGCTCATCTGGATTAATAAAGAGGAGATGATCT 110       120       130       140       150
TGGAGATCCCATGGAAGCATGCTGCCAAGCATGGCTGGGACATCAACAAG 160       170       180       190       200
GATGCCTGTTTGTTCCGGAGCTGGGCCATTCACACAGGCCGATACAAAGC 210       220       230       240       250
AGGGGAAAAGGAGCCAGATCCCAAGACGTGGAAGGCCAACTTTCGCTGTG 260       270       280       290       300
CCATGAACTCCCTGCCAGATATCGAGGAGGTGAAAGACCAGAGCAGGAAC 310       320       340       340       350
AAGGGCAGCTCAGCTGTGCGAGTGTACCGGATGCTTCCACCTCTCACCAA 360       370       380       390       400
GAACCAGAGAAAAGAAAGAAAGTCGAAGTCCAGCCGAGATGCTAAGAGCA 410       420       430       440       450
AGGCCAAGAGGAAGTCATGTGGGGATTCCAGCCCTGATACCTTCTCTGAT 460       470       480       490       500
GGACTCAGCAGCTCCACTCTGCCTGATGACCACAGCAGCTACACAGTTCC 510       520       530       540       550
AGGCTACATGCAGGACTTGGAGGTGGAGCAGGCCCTGACTCCAGCACTGT 560       570       580       590       600
CGCCATGTGCTGTCAGCAGCACTCTCCCCGACTGGCACATCCCAGTGGAA 610       620       630       640       650
GTTGTGCCGGACAGCACCAGTGATCTGTACAACTTCCAGGTGTCACCCAT 660       670       680       690       700
GCCCTCCATCTCTGAAGCTACAACAGATGAGGATGAGGAAGGGAAATTAC 710       720       730       740       750
CTGAGGACATCATGAAGCTCTTGGAGCAGTCGGAGTGGCAGCCAACAAAC 760       770       780       790       800
GTGGATGGGAAGGGGTACCTACTCAATGAACCTGGAGTCCAGCCCACCTC
```

-continued

```
           810        820        830        840        850
TGTCTATGGAGACTTTAGCTGTAAGGAGGAGCCAGAAATTGACAGCCCAG
           860        870        880        890        900
GGGGGGATATTGGGCTGAGTCTACAGCGTGTCTTCACAGATCTGAAGAAC
           910        920        930        940        950
ATGGATGCCACCTGGCTGGACAGCCTGCTGACCCCAGTCCGGTTGCCCTC
           960        970
CATCCAGGCCATTCCCTGTGCACCGTAGCAGGGCCCCTGGGCCCCTCTTA

TTCCTCTAGGCAAGCAGGACCTGGCATCATGGTGGATATGGTGCAGAGAA

GCTGGACTTCTGTGGGCCCCTCAACAGCCAAGTGTGACCCCACTGCCAAG

TGGGGATGGGCCTCCCTCCTTGGGTCATTGACCTCTCAGGGCCTGGCAGG

CCAGTGTCTGGGTTTTTCTTGTGGTGTAAAGCTGGCCCTGCCTCCTGGGA

AGATGAGGTTCTGAGACCAGTGTATCAGGTCAGGGACTTGGACAGGAGTC

AGTGTCTGGCTTTTTCCTCTGAGCCCAGCTGCCTGGAGAGGGTCTCGCTG

TCACTGGCTGGCTCCTAGGGGAACAGACCAGTGACCCCAGAAAAGCATAA

CACCAATCCCAGGGCTGGCTCTGCACTAAGAGAAAATTGCACTAAATGAA

TCTCGTTCCAAAGAACTACCCCTTTTCAGCTGAGCCCTGGGGACTGTTCC

AAAGCCAGTGAATGTGAAGGAAAGTGGGGTCCTTCGGGGCAATGCTCCCT

CAGCCTCAGAGGAGCTCTACCCTGCTCCCTGCTTTGGCTGAGGGGCTTGG

GAAAAAAACTTGGCACTTTTCGTGTGGATCTTGCCACATTTCTGATCAG

AGGTGTACACTAACATTTCCCCCGAGCTCTTGGCCTTTGCATTTATTTAT

ACAGTGCCTTGTCGCGGGCCCACCACCCCCTCAAGCCCCAGCAGCCCTCA

ACAGGCCCAGGGAGGGAAGTGTGAGCGCCTTGGTATGACTTAAAATTGGA

AATGTCATCTAACCATTAAGTCATGTGTGAACACATAAGGACGTGTGTAA

ATATGTACATTTGTCTTTTTATAAAAAGTAAAATTGTT.
```

5. The composition of claim 1, wherein the amino acid sequence of said IRF-1 comprises

| Met | Pro | Ile | Thr | Arg | Met | Arg | Met | Arg | Pro | Trp | Leu | Glu | Met | Gln | Ile |
|-----|-----|-----|-----|-----|-----|-----|-----|-----|-----|-----|-----|-----|-----|-----|-----|
| Asn | Ser | Asn | Gln | Ile | Pro | Gly | Leu | Ile | Trp | Ile | Asn | Lys | Glu | Glu | Met |
| Ile | Phe | Gln | Ile | Pro | Trp | Lys | His | Ala | Ala | Lys | His | Gly | Trp | Asp | Ile |
| Asn | Lys | Asp | Ala | Cys | Leu | Phe | Arg | Ser | Trp | Ala | Ile | His | Thr | Gly | Arg |
| Tyr | Lys | Ala | Gly | Glu | Lys | Glu | Pro | Asp | Pro | Lys | Thr | Trp | Lys | Ala | Asn |
| Phe | Arg | Cys | Ala | Met | Asn | Ser | Leu | Pro | Asp | Ale | Glu | Glu | Val | Lys | Asp |
| Gln | Ser | Arg | Asn | Lys | Gly | Ser | Ser | Ala | Val | Arg | Val | Tyr | Arg | Met | Leu |
| Pro | Pro | Leu | Thr | Arg | Asn | Gln | Arg | Lys | Glu | Arg | Lys | Ser | Lys | Ser | Ser |
| Arg | Asp | Thr | Lys | Ser | Lys | Thr | Lys | Arg | Lys | Leu | Cys | Gly | Asp | Val | Ser |
| Pro | Asp | Thr | Phe | Ser | Asp | Gly | Leu | Ser | Ser | Ser | Thr | Leu | Pro | Asp | Asp |
| His | Ser | Ser | Tyr | Thr | Thr | Gln | Gly | Tyr | Leu | Gly | Gln | Asp | Leu | Asp | Met |
| Glu | Arg | Asp | Ile | Thr | Pro | Ala | Leu | Ser | Pro | Cys | Val | Val | Ser | Ser | Ser |
| Leu | Ser | Glu | Trp | His | Met | Gln | Met | Asp | Ile | Ile | Pro | Asp | Ser | Thr | Thr |

-continued

| Asp | Leu | Tyr | Asn | Leu | Gln | Val | Ser | Pro | Met | Pro | Ser | Thr | Ser | Glu | Ala |
|---|---|---|---|---|---|---|---|---|---|---|---|---|---|---|---|
| Ala | Thr | Asp | Glu | Asp | Glu | Glu | Gly | Lys | Ile | Ala | Glu | Asp | Leu | Met | Lys |
| Leu | Phe | Glu | Gln | Ser | Glu | Trp | Gln | Pro | Thr | His | Ile | Asp | Gly | Lys | Gly |
| Tyr | Leu | Leu | Asn | Glu | Pro | Gly | Thr | Gln | Leu | Ser | Ser | Val | Tyr | Gly | Asp |
| Phe | Ser | Cys | Lys | Glu | Glu | Pro | Glu | Ile | Asp | Ser | Pro | Arg | Gly | Asp | Ile |
| Gly | Ile | Gly | Ile | Gln | His | Val | Phe | Thr | Glu | Met | Lys | Asn | Met | Asp | Ser |
| Ile | Met | Trp | Met | Asp | Ser | Leu | Leu | Gly | Asn | Ser | Val | Arg | Leu | Pro | Pro |
| Ser | Ile | Gln | Ala | Ile | Pro | Cys | Ala | Pro. | | | | | | | |

6. The composition of claim 5, wherein said nucleic acid sequence comprises

```
ATG CCA ATC ACT CGA ATG CGG ATG AGA CCC TGG CTA GAG ATG CAG ATT
AAT TCC AAG CAA ATC CCA GGG CTG ATC TGG ATC AAT AAA GAA GAG ATG
ATC TTC CAG ATT CCA TGG AAG CAC GCT GCT AAG CAC GGC TGG GAC ATC
AAC AAG GAT GCC TGT CTG TTC CGG AGC TGG GCC ATT CAC ACA GGC CGA
TAC AAA GCA GGA GAA AAA GAG CCA GAT CCC AAG ACA TGG AAG GCA AAC
TTC CGT TGT GCC ATG AAC TCC CTG CCA GAC ATC GAG GAA GTG AAG GAT
CAG AGT AGG AAC AAG GGC AGC TCT GCT GTG CGG GTG TAC CGG ATG CTG
CCA CCC CTC ACC AGG AAC CAG AGG AAA GAG AGA AAG TCC AAG TCC AGC
CGA GAC ACT AAG AGC AAA ACC AAG AAG CTG TGT GGA GAT GTT AGC
CCG GAC ACT TTC TCT GAT GGA CTC AGC AGC TCT ACC CTA CCT GAT GAC
CAC AGC AGT TAC ACC ACT CAG GGC TAC CTG GGT CAG GAC TTG GAT ATG
GAA AGG GAC ATA ACT CCA GCA CTG TCA CCG TGT GTC GTC AGC AGC AGT
CTC TCT GAG TGG CAT ATG CAG ATG GAC ATT ATA CCA GAT AGC ACC ACT
GAT CTG TAT AAC CTA CAG GTG TCA CCC ATG CCT TCC ACC TCC GAA GCC
GCA ACA GAC GAG GAT GAG GAA GGG AAG ATA GCC GAA GAC CTT ATG AAG
CTC TTT GAA CAG TCT GAG TGG CAG CCG ACA CAC ATC GAT GGC AAG GGA
TAC TTG CTC AAT GAG CCA GGG ACC CAG CTC TCT TCT GTC TAT GGA GAC
TTC AGC TGC AAA GAG GAA CCA GAG ATT GAC AGC CCT CGA GGG GAC ATT
GGG ATA GGC ATA CAA CAT GTC TTC ACG GAG ATG AAG AAT ATG GAC TCC
ATC ATG TGG ATG GAC AGC CTG CTG GGC AAC TCT GTG AGG CTG CCG CCC
TCT ATT CAG GCC ATT CCT TGT GCA CCA TAG.
```

7. The composition of claim 6, wherein said nucleic acid sequence comprises upstream and downstream sequences that flank the sequence encoding said IRF-1, and said upstream and downstream sequences and said IRF-1 encoding sequences comprise

```
  1 GGACGTGCTTTCACAGTCTAAGCCGAACCGAACCGAACCGAACCGAACCGGGCC

60 GAGTTGCGCCGAGGTCAGCCGAGGTGGCCAGAGGACCCCAGCATCTCGGGCATCTTTCG

119 CTTCGTGCGCGCATCGCGTACCTACACCGCAACTCCGTGCCTCGCTCTCCGGCACCCTC

178 TGCGAATCGCTCCTGCAGCAA     AGCCACC ATG CCA ATC ACT CGA ATG CGG

227 ATG AGA CCC TGG CTA GAG ATG CAG ATT AAT TCC AAC CAA ATC CAA

272 GGG CTG ATC TGG ATC AAT AAA GAA GAG ATG ATC TTC CAG ATT CCA

317 TGG AAG CAC GCT GCT AAG CAC GGC TGG GAC ATC AAC AAG GAT GCC

362 TGT CTG TTC CGG AGC TGG GCC ATT CAC ACA GGC CGA TAC AAA GCA

407 GGA GAA AAA GAG CCA GAT CCC AAG ACA TGG AAG GCA AAC TTC CGT

452 TGT GCC ATG AAC TCC CTG CCA GAC ATC GAG GAA GTG AAG GAT CAG

497 AGT AGG AAC AAG GGC AGC TCT GCT GTG CCG GTG TAC CGG ATG CTG
```

-continued

```
 542 CCA CCC CTC ACC AGG AAC CAG AGG AAA GAG AGA AAG TCC AAG TCC

587 AGC CGA GAC ACT AAG AGC AAA ACC AAG AGG AAG CTG TGT GGA GAT

632 GTT AGC CCG GAC ACT TTC TCT GAT GGA CTC AGC AGC TCT ACC CTA

677 CCT GAT GAC CAC AGC AGT TAC ACC ACT CAG GGC TAC CTG GGT CAG

722 GAC TTG GAT ATG GAA AGG GAC ATA ACT CCA GCA CTG TCA CCG TGT

767 GTC GTC AGC AGC AGT CTC TCT GAG TGG CAT ATG CAG ATG GAC ATT

812 ATA CCA GAT AGC ACC ACT GAT CTG TAT AAC CTA CAG GTG TCA CCC

857 ATG CCT TCC ACC TCC GAA GCC GCA ACA GAC GAG GAT GAG GAA GGG

902 AAG ATA GCC GAA GAC CTT ATG AAG CTC TTT GAA CAG TCT GAG TGG

947 CAG CCG ACA CAC ATC GAT GCC AAG GGA TAC TTG CTC AAT GAG CCA

992 GGG ACC CAG CTC TCT TCT GTC TAT GGA GAC TTC AGC TGC AAA GAG

1037 GAA CCA GAC ATT GAC AGC CCT CGA GGG GAC ATT GGG ATA GGC ATA

1082 CAA CAT GTC TTC ACG GAG ATG AAG AAT ATG GAC TCC ATC ATG TGG

1127 ATG GAC AGC CTG CTG GGC AAC TCT GTG AGG CTG CCG CCC TCT ATT

1172 CAG GCC ATT CCT TGT GCA CCA TAG   TTTGGGTCTCTGACCCGTTCTTGCCC
1222 TCCTGAGTGAGTTAGGCCTTGGCATCATGGTGGCTGTGATACAAAAAAAGCTAGACTCC
1281 TGTGGGCCCCTTGACACATGGCAAAGCATAGTCCCACTGCAAACAGGGGACCATCCTCC
1340 TTGGGTCAGTGGGCTCTCAGGGCTTAGGAGGCAGAGTCTGAGTTTTCTTGTGAGGTGAA
1399 GCTGGCCCTGACTCCTAGGAAGATGGATTGGGGGGTCTGAGGTGTAAGGCAGAGGCCAT
1458 GGACAGGAGTCATCTTCTAGCTTTTTAAAAGCCTTGTTGCATAGAGAGGGTCTTATCGC
1517 TGGGCTGGCCCTGAGGGGAATAGACCAGCGCCCACAGAAGAGCATAGCACTGGCCCTAG
1576 AGCTGGCTCTGTACTAGGAGACAATTGCACTAAATGAGTCCTATTCCCAAAGAACTGCT
1635 GCCCTTCCCAACCGAGCCCTGGGATGGTTCCCAAGCCAGTGAAATGTGAAGGGAAAAAA
1694 AATGGGGTCCTGTGAAGGTTGGCTCCCTTAGCCTCAGAGGGAATCTGCCTCACTACCTG
1753 CTCCAGCTGTGGGGCTCAGGAAAAAAAAATGGCACTTTCTCTGTGGACTTTGCCACATT
1812 TCTGATCAGAGGTGTACACTAACATTTCTCCCCAGTCTAGGCCTTTGC<u>ATTTATTTAT</u>A
1871 TAGTGCCTTGCCTGGTGCCTGCTGTCTCCTCAGGCCTTGGCAGTCCTCAGCAGGCCCAG
1930 GGAAAAGGGGGGTTGTGAGCGCCTTGGCGTGACTCTTGACTATCTATTAGAAACGCCAC
```

-continued

1989 CTAACTGCTAAATGGTGTTTGGTCATGTGGTGGACCTGTGTAAATATGTATATTTGTCT

2048 TTTTATAAAAATTTAAGTTGTTTACAAAAAAAAAA 2082.

8. The composition of any one of claims 1–7, wherein said host cell is a bacterial, yeast or mammalian cell.

9. The composition of claim 8, wherein said host cell is a bacterial cell.

10. The composition of claim 9, wherein said bacterial cell is an E. coli cell.

11. The composition of claim 8, wherein said host cell is a yeast cell.

12. The composition of claim 8, wherein said host cell is a mammalian cell.

13. The composition of claim 12, wherein said mammalian cell is a mouse cell.

14. The composition of claim 12, wherein said mammalian cell is a CHO cell.

15. Purified human IRF-1 having the amino acid sequence

MetProIleThrTrpMetArgMetArgProTrpLeuGluMet
GlnIleAsnSerAsnGlnIleProGlyLeuIleTrpIleAsnLysGluGluMetIleLeu
GluIleProTrpLysHisAlaAlaLysHisGlyTrpAspIleAsnLysAspAlaCysLeu
PheArgSerTrpAlaIleHisThrGlyArgTyrLysAlaGlyGluLysGluProAspPro
LysThrTrpLysAlaAsnPheArgCysAlaMetAsnSerLeuProAspIleGluGluVal

-continued

LysAspGlnSerArgAsnLysGlySerSerAlaValArgValTryArgMetLeuProPro
LeuThrLysAsnGlnArgLysGluArgLysSerLysSerSerArgAspAlaLysSerLys
AlaLysArgLysSerCysGlyAspSerSerProAspThrPheSerAspGlyLeuSerSer
SerThrLeuProAspAspHisSerSerTyrThrValProGlyTyrMetGlnAspLeuGlu
ValGluGlnAlaLeuThrProAlaLeuSerProCysAlaValSerSerThrLeuProAsp
TrpHisIleProValGluValValProAspSerThrSerAspLeuTyrAsnPheGlnVal
SerProMetProSerIleSerGluAlaThrThrAspGluAspGluGluGlyLysLeuPro
GluAspIleMetLysLeuLeuGluGlnSerGluTrpGlnProThrAsnValAspGlyLys
GlyTryLeuLeuAsnGluProGlyValGlnProThrSerValTyrGlyAspPheSerCys
LysGluGluProGluIleAspSerProGlyGlyAspIleGlyLeuSerLeuGlnArgVal
PheThrAspLeuLysAsnMetAspAlaThrTrpLeuAspSerLeuLeuThrProValArg
LeuProSerIleGlnAlaIleProCysAlaPro.

16. Purified murine IRF-1 having the amino acid sequence

| Met | Pro | Ile | Thr | Arg | Met | Arg | Met | Arg | Pro | Trp | Leu | Glu | Met | Gln | Ile |
|---|---|---|---|---|---|---|---|---|---|---|---|---|---|---|---|
| Asn | Ser | Asn | Gln | Ile | Pro | Gly | Leu | Ile | Trp | Ile | Asn | Lys | Glu | Glu | Met |
| Ile | Phe | Gln | Ile | Pro | Trp | Lys | His | Ala | Ala | Lys | His | Gly | Trp | Asp | Ile |
| Asn | Lys | Asp | Ala | Cys | Leu | Phe | Arg | Ser | Trp | Ala | Ile | His | Thr | Gly | Arg |
| Tyr | Lys | Ala | Gly | Glu | Lys | Glu | Pro | Asp | Pro | Lys | Thr | Trp | Lys | Ala | Asn |
| Phe | Arg | Cys | Ala | Met | Asn | Ser | Leu | Pro | Asp | Ale | Glu | Glu | Val | Lys | Asp |
| Gln | Ser | Arg | Asn | Lys | Gly | Ser | Ser | Ala | Val | Arg | Val | Tyr | Arg | Met | Leu |
| Pro | Pro | Leu | Thr | Arg | Asn | Gln | Arg | Lys | Glu | Arg | Lys | Ser | Lys | Ser | Ser |
| Arg | Asp | Thr | Lys | Ser | Lys | Thr | Lys | Arg | Lys | Leu | Cys | Gly | Asp | Val | Ser |
| Pro | Asp | Thr | Phe | Ser | Asp | Gly | Leu | Ser | Ser | Ser | Thr | Leu | Pro | Asp | Asp |
| His | Ser | Ser | Tyr | Thr | Thr | Gln | Gly | Tyr | Leu | Gly | Gln | Asp | Leu | Asp | Met |
| Glu | Arg | Asp | Ile | Thr | Pro | Ala | Leu | Ser | Pro | Cys | Val | Val | Ser | Ser | Ser |
| Leu | Ser | Glu | Trp | His | Met | Gln | Met | Asp | Ile | Ile | Pro | Asp | Ser | Thr | Thr |
| Asp | Leu | Tyr | Asn | Leu | GlN | Val | Ser | Pro | Met | Pro | Ser | Thr | Ser | Glu | Ala |
| Ala | Thr | Asp | Glu | Asp | Glu | Glu | Gly | Lys | Ile | Ala | Glu | Asp | Leu | Met | Lys |
| Leu | Phe | Glu | Gln | Ser | Glu | Trp | Gln | Pro | Thr | His | Ile | Asp | Gly | Lys | Gly |
| Tyr | Leu | Leu | Asn | Glu | Pro | Gly | Thr | GlN | Leu | Ser | Ser | Val | Tyr | Gly | Asp |
| Phe | Ser | Cys | Lys | Glu | Glu | Pro | Glu | Ile | Asp | Ser | Pro | Arg | Gly | Asp | Ile |
| Gly | Ile | Gly | Ile | Gln | His | Val | Phe | Thr | Glu | Met | Lys | Asn | Met | Asp | Ser |
| Ile | Met | Trp | Met | Asp | Ser | Leu | Leu | Gly | Asn | Ser | Val | Arg | Leu | Pro | Pro |
| Ser | Ile | Gln | Ala | Ile | Pro | Cys | Ala | Pro. | | | | | | | |

\* \* \* \* \*

UNITED STATES PATENT AND TRADEMARK OFFICE
CERTIFICATE OF CORRECTION

PATENT NO. : 5,831,006

DATED : November 3, 1998

INVENTORS : Taniguchi *et al.*

It is certified that an error appears in the above-identified patent and that said Letters Patent is hereby corrected as shown below.

Title page, column 1, Item [73] Assignee, please delete "Takashi Fujita," and insert therein --Tadasugu Taniguchi,--.

Column 18, Formula VI, for every instance where "GIN" appears please delete "GIN" and insert therein --Gln--.

Column 45, claim 5 (continued), for every instance where "GIN" appears please delete "GIN" and insert therein --Gln--.

Column 50, claim 16, for every instance where "GIN" appears please delete "GIN" and insert therein --Gln--.

Signed and Sealed this

Twenty-third Day of November, 1999

Attest:

Q. TODD DICKINSON

*Attesting Officer*  *Acting Commissioner of Patents and Trademarks*